United States Patent [19]

Pusztai et al.

[11] Patent Number: 6,110,891
[45] Date of Patent: Aug. 29, 2000

[54] LECTIN COMPOSITIONS AND USES THEREOF

[75] Inventors: Arpad Janos Pusztai; Zsuzsanna Magdolna Bardocz, both of Scotland; Richard Michael John Palmer; Neil William Fish, both of England, all of United Kingdom; Gyorgy J. Koteles, Budapest, Hungary

[73] Assignee: Alizyme Therapeutics Ltd., Cambridge, United Kingdom

[21] Appl. No.: 09/141,821

[22] Filed: Aug. 28, 1998

Related U.S. Application Data

[63] Continuation-in-part of application No. 08/994,288, Dec. 19, 1997, which is a continuation-in-part of application No. 08/879,761, Jun. 20, 1997, abandoned.

[30] Foreign Application Priority Data

Jun. 21, 1996 [GB] United Kingdom .................... 9613070
Aug. 29, 1997 [GB] United Kingdom .................... 9718413

[51] Int. Cl.[7] ..................................................... A61K 38/16
[52] U.S. Cl. .................. 514/8; 514/2; 514/922; 514/925; 514/926; 514/927
[58] Field of Search .................................. 514/2, 8, 922, 514/925, 926, 927

[56] References Cited

U.S. PATENT DOCUMENTS

| 4,742,046 | 5/1988 | Bliah | 514/8 |
|---|---|---|---|
| 5,102,870 | 4/1992 | Florine et al. | 514/12 |
| 5,840,771 | 11/1998 | Oldham et al. | 514/931 |

FOREIGN PATENT DOCUMENTS

| 87-024774 | 12/1986 | United Kingdom . |
|---|---|---|
| 94-157940 | 3/1993 | United Kingdom . |

OTHER PUBLICATIONS

Josiane Wantyghem et al., "Purification and Characterization of Robinia Pseudoacacia Seed Lectins", *The Biochemical Journal*, vol. 237, No. 2, Jul. 15, 1986, pp. 483–489.

*Primary Examiner*—Frederick Krass
*Attorney, Agent, or Firm*—Peter F. Corless; Christine C. O'Day; Dike, Bronstein, Roberts & Cushman, LLP

[57] ABSTRACT

This invention provides methods for: the control of mucosal cell proliferation; the reduction and/or treatment of damage caused by a cell-damaging agent; and for the reduction and/or treatment of a metabolic disorder.

The methods comprise administering to an individual in need of control or reduction and/or treatment on effective amount of a lectin.

The invention takes advantageous of the protective and repair capabilities of lectins. It is particularly useful in the prevention and treatment of animals undergoing radiotherapy and/or chemotherapy for cancer.

75 Claims, 7 Drawing Sheets

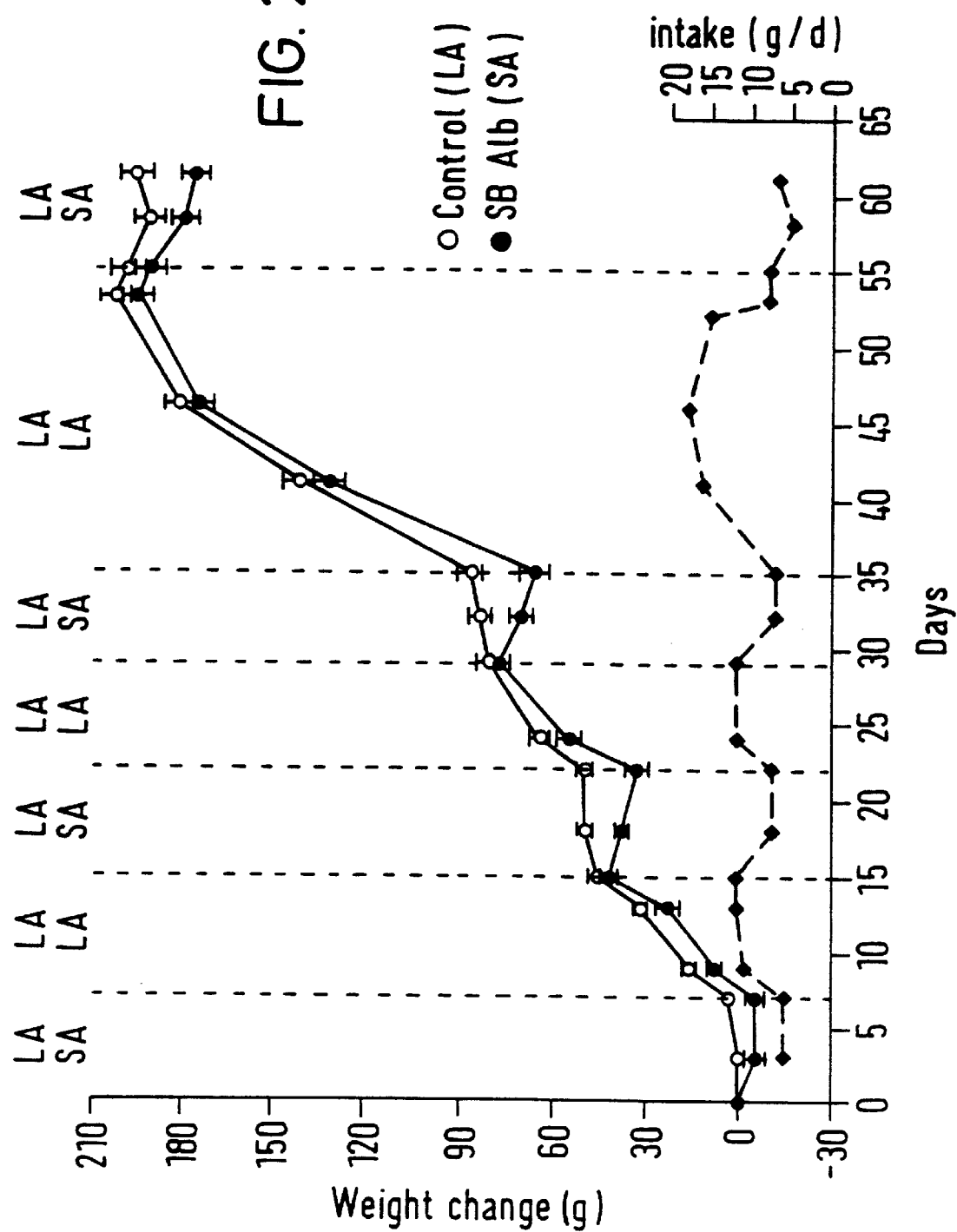

Predicted amino acid sequences of lectin cDNA clones from Robinia pseudoacacia bark

```
              -31                                                    1                    14

Polypeptide a:   MTSYNFKTQTSFLLLLSISFFFLLLLN .. KVNS   TGSLSFSFPKFAPN
Polypeptide b:   MASYKFKTQNSFLLLLSISFFFLLLLN .. KVNS   TGSLSFSFPKFKHS
Polypeptide c:            PFNPETVYALLAMLISFFVLLASARKENS  DEGISFNFTNFTRG

66

Polypeptide a:   QPYLIFQRDALVTSTGVLQLTNVVNGVPSGKSLGRALYAAPFQIWDSTTGNV
Polypeptide b:   QPDLIFQSDALVTSKGVLQLTTVNDGRVYD-SIGRVLYAAPFQIWDSTTGNV
Polypeptide c:   DQGVTLLGQANIMANGILALTN... HTNPTWNT.GRALYSKPVPIWDSATGNV

117

Polypeptide a:   ASFVTSFSFIIQAPNPTTTADGLAFFLAPVD . TPQLDVGGMLGIFKDGYFNK
Polypeptide b:   ASFVTSFSFIIKAPNEGKTADGLVFFLAPVGSTQPLKGGGLLGLFKDESYNK
Polypeptide c:   ASFVTSFSFVVKEIKGGIPADGIVFFLAPEARIPDNSAGGQLGIVNAN..KA

167

Polypeptide a:   SNQIVAVEFDTFSNIHFDPK.GRHMGDNVNSIVSIKTVPWNWTNGEVANVF
Polypeptide b:   SNQIVAVEFDTFRNVAWDPN..GIHMGIDVNSIQSVRTVRWDWANGEVANVF
Polypeptide c:   YNPFVGVEFDTYSN.NWDPK..SAHIGIDASSLISLRTVKWNKVSGSLVKVS

219

Polypeptide a:   ISYEASTKSLTASLVYPSLETSFIVHAIVDVKDVLPEWVRFGFSATTGIDKG
Polypeptide b:   ISYEASTKSLTASLVYPSLEKSFILSAIVDLKKVLPEWVRVGFTATTGLSED
polypeptide c:   IIYDSLSKTLSVVVTHENGQIS . TIAQVVDLKAVLGEKVRVGFTAATTTGR.

254

Polypeptide a:   YVQTNDVLSWSFESNLPGGNSVASVKNAGLSTYAA
Polypeptide b:   YVQTNDVLSWSFESNLPGGNSVASVKNAGLSTYAA
Polypeptide c:   YVELYDIHAWSFTSTLVTATSSTS . KNMNIASAA
```

FIGURE 6

Predicted amino acid sequences of lectin cDNA from Robinia pseudoacacia seed.

```
             -31                                      1
                                                                                14
   RPsAI:    kaMASYKFKTQNSFPLLLSISFFFLLLLN..KVNS  TGSLSFSFPKFAPN
   RPsAII:   naMASYKFKTQNSFLLLLSISFFFLLLLN..KVNS  TGSLSFSFPKFAPN

66
   RPsAI:    QPYLIFQRDALVTSTGVLQLTNVVNGVPPRRSIGRALYAAPFQIWDNTTGNV
   RPsAII:   QPYLIFQRDALVTSTGVLQLTNVVNGVPSRKSLGRALYAAPFQIWDSTTGNV

117
   RPsAI:    ASFVTSFSFIIQAPNPATTADGLAFFLAPVD.TQPGDLGGMLGIFKDGSYNK
   RPsAII:   ASFVTSFSFIIQAPNPATTADGLAFFLAPVD.TQPLDLGGMLGIFKNGYFNK

167
   RPsAI:    SNQIVAVEFDTFSNIHFDPK..GRHMGINVNSIVSVKTVPWNWTNGEVANVF
   RPsAII:   SNQIVAVEFDTFSNRHWDPT..GRHMGINVNSIVSVKTVPWNWANGEVANVF

219
   RPsAI:    ISYEASTKSLNASLVYPSLETSFIIHAIVDVKDVLPEWVRFGFSATTGIDTG
   RPsAII:   ISYEASTKSLTASLVYPSLETSFIIHAIVDVKDVLPEWVRFGFSATTGIDTG

254
   RPsAI:    YVQTNDVLSWSFESNLPGGNSVASVKNAGLSTYAA
   RPsAII:   YVQTNDVLSWSFESNLPGGNSVASVKNAGLSTYAA
```

FIGURE 7

```
                            SEQUENCE LISTING

<160> NUMBER OF SEQ ID NOS: 5

<210> SEQ ID NO 1
<211> LENGTH: 285
<212> TYPE: PRT
<213> ORGANISM: Human

<400> SEQUENCE: 1

Met Thr Ser Tyr Asn Phe Lys Thr Gln Thr Ser Phe Leu Leu Leu Leu
 1               5                  10                  15

Ser Ile Ser Phe Phe Leu Leu Leu Leu Asn Lys Val Asn Ser Thr
            20                  25                  30

Gly Ser Leu Ser Phe Ser Phe Pro Lys Phe Ala Pro Asn Gln Pro Tyr
        35                  40                  45

Leu Ile Phe Gln Arg Asp Ala Leu Val Thr Ser Thr Gly Val Leu Gln
```

```
            50                  55                  60
Leu Thr Asn Val Val Asn Gly Val Pro Ser Gly Lys Ser Leu Gly Arg
 65                  70                  75                  80

Ala Leu Tyr Ala Ala Pro Phe Gln Ile Trp Asp Ser Thr Thr Gly Asn
                 85                  90                  95

Val Ala Ser Phe Val Thr Ser Phe Ser Phe Ile Ile Gln Ala Pro Asn
            100                 105                 110

Pro Thr Thr Thr Ala Asp Gly Leu Ala Phe Phe Leu Ala Pro Val Asp
            115                 120                 125

Thr Pro Gln Leu Asp Val Gly Gly Met Leu Gly Ile Phe Lys Asp Gly
            130                 135                 140

Tyr Phe Asn Lys Ser Asn Gln Ile Val Ala Val Glu Phe Asp Thr Phe
145                 150                 155                 160

Ser Asn Ile His Phe Asp Pro Lys Gly Arg His Met Gly Ile Asn Val
                165                 170                 175

Asn Ser Ile Val Ser Ile Lys Thr Val Pro Trp Asn Trp Thr Asn Gly
            180                 185                 190

Glu Val Ala Asn Val Phe Ile Ser Tyr Glu Ala Ser Thr Lys Ser Leu
            195                 200                 205

Thr Ala Ser Leu Val Tyr Pro Ser Leu Glu Thr Ser Phe Ile Val His
            210                 215                 220

Ala Ile Val Asp Val Lys Asp Val Leu Pro Glu Trp Val Arg Phe Gly
225                 230                 235                 240

Phe Ser Ala Thr Thr Gly Ile Asp Lys Gly Tyr Val Gln Thr Asn Asp
                245                 250                 255

Val Leu Ser Trp Ser Phe Glu Ser Asn Leu Pro Gly Gly Asn Ser Val
            260                 265                 270

Ala Ser Val Lys Asn Ala Gly Leu Ser Thr Tyr Ala Ala
            275                 280                 285

<210> SEQ ID NO 2
<211> LENGTH: 285
<212> TYPE: PRT
<213> ORGANISM: Human

<400> SEQUENCE: 2

Met Ala Ser Tyr Lys Phe Lys Thr Gln Asn Ser Phe Leu Leu Leu Leu
  1               5                  10                  15

Ser Ile Ser Phe Phe Phe Leu Leu Leu Asn Lys Val Asn Ser Thr
                 20                  25                  30

Gly Ser Leu Ser Phe Ser Phe Pro Lys Phe Lys His Ser Gln Pro Asp
             35                  40                  45

Leu Ile Phe Gln Ser Asp Ala Leu Val Thr Ser Lys Gly Val Leu Gln
 50                  55                  60

Leu Thr Thr Val Asn Asp Gly Arg Val Tyr Asp Ser Ile Gly Arg Val
 65                  70                  75                  80

Leu Tyr Ala Ala Pro Phe Gln Ile Trp Asp Ser Thr Thr Gly Asn Val
                 85                  90                  95

Ala Ser Phe Val Thr Ser Phe Ser Phe Ile Ile Lys Ala Pro Asn Glu
            100                 105                 110

Gly Lys Thr Ala Asp Gly Leu Val Phe Phe Leu Ala Pro Val Gly Ser
            115                 120                 125

Thr Gln Pro Leu Lys Gly Gly Gly Leu Leu Gly Leu Phe Lys Asp Glu
            130                 135                 140
```

```
Ser Tyr Asn Lys Ser Asn Gln Ile Val Ala Val Glu Phe Asp Thr Phe
145                 150                 155                 160

Arg Asn Val Ala Trp Asp Pro Asn Gly Ile His Met Gly Ile Asp Val
                165                 170                 175

Asn Ser Ile Gln Ser Val Arg Thr Val Arg Trp Asp Trp Ala Asn Gly
            180                 185                 190

Glu Val Ala Asn Val Phe Ile Ser Tyr Glu Ala Ser Thr Lys Ser Leu
        195                 200                 205

Thr Ala Ser Leu Val Tyr Pro Ser Leu Glu Lys Ser Phe Ile Leu Ser
    210                 215                 220

Ala Ile Val Asp Leu Lys Lys Val Leu Pro Glu Trp Val Arg Val Gly
225                 230                 235                 240

Phe Thr Ala Thr Thr Gly Leu Ser Glu Asp Tyr Val Gln Thr Asn Asp
                245                 250                 255

Val Leu Ser Trp Ser Phe Glu Ser Asn Leu Pro Gly Gly Asn Ser Val
                260                 265                 270

Ala Ser Val Lys Asn Ala Gly Leu Ser Thr Tyr Ala Ala
            275                 280                 285

<210> SEQ ID NO 3
<211> LENGTH: 274
<212> TYPE: PRT
<213> ORGANISM: Human

<400> SEQUENCE: 3

Pro Phe Asn Pro Glu Thr Val Tyr Ala Leu Leu Ala Met Leu Ile Ser
1               5                   10                  15

Phe Phe Val Leu Leu Ala Ser Ala Arg Lys Glu Asn Ser Asp Glu Gly
            20                  25                  30

Ile Ser Phe Asn Phe Thr Asn Phe Thr Arg Gly Asp Gln Gly Val Thr
        35                  40                  45

Leu Leu Gly Gln Ala Asn Ile Met Ala Asn Gly Ile Leu Ala Leu Thr
50                  55                  60

Asn His Thr Asn Pro Thr Trp Asn Thr Gly Arg Ala Leu Tyr Ser Lys
65                  70                  75                  80

Pro Val Pro Ile Trp Asp Ser Ala Thr Gly Asn Val Ala Ser Phe Val
                85                  90                  95

Thr Ser Phe Ser Phe Val Val Lys Glu Ile Lys Gly Gly Ile Pro Ala
            100                 105                 110

Asp Gly Ile Val Phe Phe Leu Ala Pro Glu Ala Arg Ile Pro Asp Asn
        115                 120                 125

Ser Ala Gly Gly Gln Leu Gly Ile Val Asn Ala Asn Lys Ala Tyr Asn
    130                 135                 140

Pro Phe Val Gly Val Glu Phe Asp Thr Tyr Ser Asn Asn Trp Asp Pro
145                 150                 155                 160

Lys Ser Ala His Ile Gly Ile Asp Ala Ser Ser Leu Ile Ser Leu Arg
                165                 170                 175

Thr Val Lys Trp Asn Lys Val Ser Gly Ser Leu Val Lys Val Ser Ile
            180                 185                 190

Ile Tyr Asp Ser Leu Ser Lys Thr Leu Ser Val Val Val Thr His Glu
        195                 200                 205

Asn Gly Gln Ile Ser Thr Ile Ala Gln Val Val Asp Leu Lys Ala Val
    210                 215                 220

Leu Gly Glu Lys Val Arg Val Gly Phe Thr Ala Ala Thr Thr Thr Gly
225                 230                 235                 240
```

```
Arg Tyr Val Glu Leu Tyr Asp Ile His Ala Trp Ser Phe Thr Ser Thr
                245                 250                 255

Leu Val Thr Ala Thr Ser Ser Thr Ser Lys Asn Met Asn Ile Ala Ser
            260                 265                 270

Ala Ala

<210> SEQ ID NO 4
<211> LENGTH: 285
<212> TYPE: PRT
<213> ORGANISM: Human

<400> SEQUENCE: 4

Met Ala Ser Tyr Lys Phe Lys Thr Gln Asn Ser Phe Pro Leu Leu Leu
  1               5                  10                  15

Ser Ile Ser Phe Phe Leu Leu Leu Asn Lys Val Asn Ser Thr
             20                  25                  30

Gly Ser Leu Ser Phe Ser Phe Pro Lys Phe Ala Pro Asn Gln Pro Tyr
             35                  40                  45

Leu Ile Phe Gln Arg Asp Ala Leu Val Thr Ser Thr Gly Val Leu Gln
 50                  55                  60

Leu Thr Asn Val Val Asn Gly Val Pro Pro Arg Arg Ser Ile Gly Arg
 65                  70                  75                  80

Ala Leu Tyr Ala Ala Pro Phe Gln Ile Trp Asp Asn Thr Thr Gly Asn
                 85                  90                  95

Val Ala Ser Phe Val Thr Ser Phe Ser Phe Ile Ile Gln Ala Pro Asn
                100                 105                 110

Pro Ala Thr Thr Ala Asp Gly Leu Ala Phe Phe Leu Ala Pro Val Asp
            115                 120                 125

Thr Gln Pro Gly Asp Leu Gly Gly Met Leu Gly Ile Phe Lys Asp Gly
130                 135                 140

Ser Tyr Asn Lys Ser Asn Gln Ile Val Ala Val Glu Phe Asp Thr Phe
145                 150                 155                 160

Ser Asn Ile His Phe Asp Pro Lys Gly Arg His Met Gly Ile Asn Val
                165                 170                 175

Asn Ser Ile Val Ser Val Lys Thr Val Pro Trp Asn Trp Thr Asn Gly
            180                 185                 190

Glu Val Ala Asn Val Phe Ile Ser Tyr Glu Ala Ser Thr Lys Ser Leu
        195                 200                 205

Asn Ala Ser Leu Val Tyr Pro Ser Leu Glu Thr Ser Phe Ile Ile His
210                 215                 220

Ala Ile Val Asp Val Lys Asp Val Leu Pro Glu Trp Val Arg Phe Gly
225                 230                 235                 240

Phe Ser Ala Thr Thr Gly Ile Asp Thr Gly Tyr Val Gln Thr Asn Asp
                245                 250                 255

Val Leu Ser Trp Ser Phe Glu Ser Asn Leu Pro Gly Gly Asn Ser Val
            260                 265                 270

Ala Ser Val Lys Asn Ala Gly Leu Ser Thr Tyr Ala Ala
        275                 280                 285

<210> SEQ ID NO 5
<211> LENGTH: 285
<212> TYPE: PRT
<213> ORGANISM: Human

<400> SEQUENCE: 5
```

-continued

```
Met Ala Ser Tyr Lys Phe Lys Thr Gln Asn Ser Phe Leu Leu Leu
1               5                   10                  15

Ser Ile Ser Phe Phe Phe Leu Leu Leu Asn Lys Val Asn Ser Thr
            20              25              30

Gly Ser Leu Ser Phe Ser Phe Pro Lys Phe Ala Pro Asn Gln Pro Tyr
        35              40              45

Leu Ile Phe Gln Arg Asp Ala Leu Val Thr Ser Thr Gly Val Leu Gln
    50              55              60

Leu Thr Asn Val Val Asn Gly Val Pro Ser Arg Lys Ser Leu Gly Arg
65              70              75              80

Ala Leu Tyr Ala Ala Pro Phe Gln Ile Trp Asp Ser Thr Thr Gly Asn
            85              90              95

Val Ala Ser Phe Val Thr Ser Phe Ser Phe Ile Ile Gln Ala Pro Asn
            100             105             110

Pro Ala Thr Thr Ala Asp Gly Leu Ala Phe Phe Leu Ala Pro Val Asp
            115             120             125

Thr Gln Pro Leu Asp Leu Gly Gly Met Leu Gly Ile Phe Lys Asn Gly
    130             135             140

Tyr Phe Asn Lys Ser Asn Gln Ile Val Ala Val Glu Phe Asp Thr Phe
145             150             155             160

Ser Asn Arg His Trp Asp Pro Thr Gly Arg His Met Gly Ile Asn Val
            165             170             175

Asn Ser Ile Val Ser Val Lys Thr Val Pro Trp Asn Trp Ala Asn Gly
            180             185             190

Glu Val Ala Asn Val Phe Ile Ser Tyr Glu Ala Ser Thr Lys Ser Leu
        195             200             205

Thr Ala Ser Leu Val Tyr Pro Ser Leu Glu Thr Ser Phe Ile Ile His
    210             215             220

Ala Ile Val Asp Val Lys Asp Val Leu Pro Glu Trp Val Arg Phe Gly
225             230             235             240

Phe Ser Ala Thr Thr Gly Ile Asp Thr Gly Tyr Val Gln Thr Asn Asp
            245             250             255

Val Leu Ser Trp Ser Phe Glu Ser Asn Leu Pro Gly Gly Asn Ser Val
            260             265             270

Ala Ser Val Lys Asn Ala Gly Leu Ser Thr Tyr Ala Ala
        275             280             285
```

LECTIN COMPOSITIONS AND USES THEREOF

This application is a continuation-in-part of U.S. Ser. No. 08/994,288, filed Dec. 19, 1997, which is a continuation-in-part of U.S. Ser. No. 08/879,761, filed Jun. 20, 1997 and now abandoned.

FIELD OF INVENTION

The invention relates to use of lectins in the manufacture of medicaments for the control of mucosal cell proliferation, for the reduction and/or treatment of damage caused by a cell-damaging agent and for the reduction and/or treatment of metabolic disorders, as well as compositions and diets comprising lectins, their use in medical and non-medical fields and the use of soya waste products, in particular the soya whey fraction, in the manufacture of the above medicaments and compositions.

BACKGROUND OF THE INVENTION

Lectins are proteins or glycoproteins, typically of plant or even microbial or animal origin which recognise and attach to specific glycoconjugate structures. Orally administered lectins such as kidney bean (*Phaseolus vulgaris*) lectin, phytohaemagglutinin (PHA), can be powerful extraneous growth factors for the rat gut, inducing fully reversible, polyamine-dependent, hyperplastic growth of the small intestine (Bardocz et al., 1992). The lectin avidly binds to the brush border and is partially transcytosed into the circulation (Pusztai, 1991). At particular doses, lectins such as PHA damage the gut wall, causing coliform overgrowth in the lumen (Pusztai et al., 1993), increasing the rate of lipid mobilisation and glucose oxidation (Grant et al., 1987) and significantly reducing the fractional rate of protein synthesis in skeletal muscle (Palmer et al., 1987; Bardocz et al., 1992). Thus, lectins such as PHA are generally regarded as nutritional toxins because at high oral doses they induce several losses of body lipids, glycogen and muscle protein (Pusztai, 1991) and possibly death.

Safe, non-toxic threshold levels for the oral administration of lectins in human and other animals are not known.

Mucosal cells are those which make up any mucous membrane (the moist membrane lining many tubular structures). Many are cells which provide a protective layer between the external environment and the internal organs of an animal. Examples of mucosal cells include the epithelial cells of the skin, the mucosal cells of the alimentary canal and the tissue covering the eye. A member of disorders of mucosal cells are known, including conditions where cell division is accelerated, decelerated, where the mucosal cells are damaged, or the protective outer layer such as mucous is missing. Conditions related to abnormal control of mucosal cell proliferation may include skin cancers, psoriasis, irritable bowel disease and mucositis. Mucositis is a painful and debilitating condition in which rapidly growing epithelial cells are damaged and the external mucous layer is removed and/or not replaced sufficiently quickly. Mucositis may result in infection by microorganisms which are present, for example in the mouth or gut. The condition is seen as a major side effect in the treatment of cancer. The incidence and severity of mucositis may increase with increasing rounds of cancer therapy, and may ultimately effect patient treatment compliance and survival.

Agents which damage mucosal (and other) cells include chemotherapeutic agents, radiotherapy, chemicals (organic and inorganic), toxins, acids, alkali, any radiation source and free radicals. Chemotherapy and radiotherapy, used either alone, used together or in combination with surgery are the main therapeutic approaches for the treatment of cancer. Chemotherapy uses a cytotoxic agent to directly damage the DNA of a target cell. If a sufficient dose of the cytotoxic agent is administered to a target tissue i.e. a tumour, DNA mis-repair may result in the accumulation of DNA mutations, lesions and chromosomal aberrations that ultimately result in cell death. Radiotherapy uses radiation to either damage the DNA of a target cell directly, or exploits the potential of ionising radiation to produce free radicals which are able to break DNA strands (Steel, 1996).

The principle by which chemotherapy is used to treat cancer is that a cytotoxic drug is administered to inhibit cell division, which may ultimately lead to cell death. As the cancerous cells are usually growing more rapidly than normal tissue, the expectation is that the cytotoxic drug will kill more cancerous cells than normal cells. Unlike radiotherapy however, the cytotoxic drugs are given in such a manner that they act systemically throughout the body. Serious side effects, such as toxicity to vital tissues including bone marrow and white blood cells may limit the dose of cytotoxic drug that can be administered without killing the patient. In a similar manner, the use of radiation to treat cancer does not discriminate between cancerous and normal tissue. The use of radiotherapy is therefore a compromise in trying to induce most damage to the cancerous cells by targeting the radiation without irreparably destroying normal tissue.

Many cytotoxic drugs have been developed and evaluated for the treatment of cancer. The main principle by which these drugs act is that they interfere or inhibit key steps in the cell division pathway. The major drug classes target either DNA replication, DNA repair, chromosome separation or cytoplasmic division. The vast majority of cytotoxic drugs interfere with the synthesis and replication of DNA. 5-fluorouracil (5-FU) and its related analogs are some of the most commonly used cytotoxic drugs in this class. The activity of 5-FU can also be modulated by the addition of reduced folates such as calcium leucovorin (Isacoff et al, 1994). Other cytoxic drugs that inhibit DNA synthesis and replication are known which target different deoxyribonucleotides used to make DNA e.g. cytarabine. DNA strands containing cytarabine directly inhibit the activity of DNA polymerase (Archimund & Thomas, 1994).

A second major class of cytotoxic drugs are those which induce the breakage of DNA strands directly, or those which inhibit the repair of DNA breaks. Cyclophosphamide is an example of a drug that can break DNA strands directly (Sparano & Wiernik, 1994). A third major class of drugs are those that actually disrupt the assembly and disassembly of tubulin, so inhibiting mitosis and cell division directly. Taxanes such as paclitaxel and docetaxel are drugs which polymerise tubular into stable microtubule bundles. Synthetic vinca-alkaloids such as vinorelbine are spindle poisons which exert their anti-tumour effects by preventing the assembly of tubulin into microtubules (Dieras & Pouillart, 1995).

Current radiotherapy practice uses a range of irradiation sources to treat cancer. The most commonly used sources are X-ray, gamma ray, proton or neutron sources of $\alpha$ or $\beta$ emitters. In practice, continuous low dose radiotherapy over several days gives the best changes of discriminating between normal and cancerous tissue. However, this technique is limited to the use of radio-isotopes which are currently only effective with a few tumour types, e.g. thyroid cancer. In the clinical situation, most radiotherapy techniques use high doses of radiation which are focused as a beam at the cancerous tissue. Exposure of normal tissue is reduced, where possible, by the use of lead shielding or by rotating the patient such that normal tissue receives a lower dose than the cancerous tissue. Although this approach can be effective, its use may be limited by cumulative exposures of normal tissue to radiation and the resistance of many tumours to high doses of radiation.

It is well known in the art that single cytotoxic agents or radiation sources may be more suitable for certain cancer types. For example, Cisplatin is widely used for testicular cancer, taxanes are more suitable for breast cancer and 5-FU is widely used for colorectal cancers. However, single agent therapies rarely provide a complete cure for cancer and rates of survival are still low. Some improvements have been made in the use of cytotoxic drug cocktails with the use of multiple drug regimes (Au et al, 1996).

A number of compounds have been evaluated in the art for their ability to sensitise cancer cells to the effects of radiation and chemotherapy (so sparing normal tissue). However, the use of radiosensitisers such as vitamin K mimetics Synkavit and Menadione and protectants such as the sulphidryl containing compounds cysteine, cysteamine and Ethylol have also been disappointing (Denekamp, 1996).

Although chemotherapy and radiotherapy are the most widely used treatments for cancer, the rates of survival are limited due to a number of factors. The key factor is that the cytotoxic drug or radiation does not discriminate between normal and cancerous tissue. In most cases, it is impossible to give a sufficient dose of cytotoxic drug or radiation to reliable kill all cancerous tissue as it would prove fatal to the patient. Common side effects for existing therapy regimes include hair loss, bone marrow suppression, nausea, vomiting and diarrhoea (Paulsen et al 1996). In addition, there are also many instances where the use of radiotherapy, particularly to the pelvic regions has resulted in altered gastrointestinal function (Yeoh et al 1993) and long term damage to the gut which requires surgery (van Halteren et al 1993).

A major breakthrough has been made in the last 10 years with the availability of hematopoetic growth factors. It is now possible to give higher doses of cytotoxic drugs and radiation and then rescue tissues such as bone marrow and white blood cells by the administration of recombinant growth factors such as granulocyte-macrophage colony-stimulating factor (Erkisis et al, 1996). Such an approach has enabled improved prognosis and survival rates to be achieved. Whilst epidermal-specific growth factors such as epidermal growth factor are known, the complex nature of gut growth regulation has made it difficult to develop effective gut "rescue" procedures (Podolsky, 1993), As no such growth factor currently exists for the gut, damage to the gastrointestinal tract by cytotoxic drugs and radiation has now become dose limiting.

The present invention utilises the tissue protecting qualities and the metabolic effects of low doses of lectins to protect and repair biological material damaged by radiotherapy and/or chemotherapy. The present invention is of particular interest because of the noted prophylactic effects of lectin compositions (positive growth factors) before treatments such as radiotherapy and/or chemotherapy.

Diseased and damaged cells, which cannot repair or regenerate sufficiently quickly can cause serious and potentially life-threatening health risks. Also a problem in maintaining normal cell functions are metabolic diseases, such as obesity, hyperglycemia, cardiovascular disease, stroke and gastrointestinal disease, including irritable bowel syndrome, inflammatory bowel disease and coeliac disease.

Metabolic disorders include any disorder which is related to and/or a result of the metabolism of the body, in particular obesity and obesity related disorders such as hyperglycaemia, (type II diabetes), cardiovascular, stroke, gastro-intestinal and gastro-intestinal related conditions. A metabolic disorder may require the control of mucosal cell proliferation, or the control of mucosal cell proliferation may be independent of a metabolic disorder.

It is known in the art that high doses of lectins can be detrimental to the metabolism of an animal. For example, high doses of lectins may interfere with the thymus, cause hypertrophy of the pancreas and coliform overgrowth resulting in poor nutrition and growth. The present invention describes for the first time, the beneficial metabolic effects of orally administering low doses of lectins. Surprisingly, it has been found that administration of low lectin doses results in a reduction in body fat content and this can be used as a treatment for obesity and for non-medically related weight loss.

The use of soya in human food is on the increase and soya proteins often supply the bulk of dietary protein in animal nutrition. Unfortunately, as soya contains a number of antinutrients, mainly lectins and trypsin inhibitors, the efficiency of nutritional utilisation of diets containing soya products is below that expected from chemical composition (Gupta, 1987), particularly when these are fed for long periods (Rackis et al, 1986) and with soya whey containing most of the soya antinutrients (Grant et al., 1986). It is a commonly held view that soya products could be more extensively used in both human and animal diets if their antinutritional effects were reduced.

The antinutrient content of most soya products is generally removed by processing based on various methods of heat-treatments (Liener, 1994). However, most of these are expensive and can lead to losses of essential amino acids and production of toxic by-products. Although cheaper and more efficient heat-processing may eventually be developed, other options for reducing the antinutritional effects of soya products include diet manipulation and the design of new feeding strategies. Rendering soya products and particularly its little-used whey fraction free of the main negative effects of antinutrients could bring considerable economical benefits to the feed industry and animal producers.

A particular lectin to which the present invention relates, for all aspects, is *Robinia pseudoacacia* (black locust, also RPA). RPA is a leguminous tree species that is common in North America and Central Europe. *Robinia pseudoacacia* produces lectins in its bark, roots, root nodules, phloem, wood and leaves (Geitle and Ziegler 1980) and in the seeds (Van Damme et al 1995b). Although the precise function of the lectins is unknown, it is believed that the lectins may be used as a store for nitrogen in dormant periods (Yoshida et al 1994). It is also known that the level of lectin within the bark increases during winter. Given the known toxicity of Robinia lectins to mammals, (Nishiguchi et al 1997) it is also possible that the bark lectin may act as a defence mechanism against herbivores such as rabbits during winter.

The bark and seed lectins of *Robinia pseudoacacia* have been characterised at both the biochemical and molecular levels (Van Damme et al., 1995a, 1995b). Root lectin has also been isolated and characterised (Duverger et al 1997). *Robinia pseudoacacia* lectins (predominantly seed derived) have had a number of uses, primarily as diagnostic and research tools. The specific carbohydrate binding properties (N-acetyl-D-galactosamine) of RPA have been used to investigate the carbohydrate composition of biological tissue (Raedler et al 1982). The mitogenic properties of RPA have also been used in in vitro studies to investigate the biology of isolated lymphocytes (Sabeur et al 1986, Sharif et al 1978 & 1977). Banach et al (1983) showed that intraperitoneal doses of RPA in mice induced a hepatotoxic effect including a rapid fall in liver glycogen. Pusztai (1993) also showed that RPA bound strongly to the gut wall of the rat and induced pancreatic growth at high doses suggesting that RPA may damage the gut wall, promote coliform overgrowth and induce pancreatitis.

The lectins from the bark of *Robinia pseudoacacia* can be characterised using a range of gel separation, DNA and protein sequencing technique (Van Damme et al 1995a). Native bark lectin eluated from a column consists of two lectins, RPbAI and RPbAII which co-purify at an apparent molecular weight of 120 kDa. Analysis of the RPbAI on an SDS PAGE gel indicates that it is composed of two subunits, polypeptide a and polypeptide b, with molecular weights of 31.5 and 29 kDa respectively. RPbAI is a tetramer composed of all the possible combinations of the a and b polypeptide monomers. Polypeptides a and b have been further characterised by cDNA cloning and sequencing using standard techniques. The predicted protein sequences of polypeptides a and b are shown in FIG. 1.

RPbAII is a tetramer composed of a single monomer polypeptide (subunit) c of 26 kDa molecular weight. Polypeptide c has been further characterised and the cDNa sequenced and the predicted protein sequence is also shown in FIG. 1.

*Robinia pseudoacacia* seed contains two lectins, RPsAI and RPsAII which co-purify at an apparent molecular weight of 120 kDa (Van Damme et al., 1995b).

Analysis of both lectins on SDS PAGE indicates that they are each comprised of a single monomer subunit (34 and 29 kDa respectively). The seed lectins have been characterised by cDNA cloning and sequencing techniques and the predicted protein sequence is shown in FIG. 2. Recently published work on the root lectins has shown that they are composed of two lectins (Duverger et al, 1997). The root lectins appear to differ from those of seed and bark in that they are dimer molecules classified as RPrAI and RPrAII of molecular weights 58 and 63 kDa respectively. RPrAI is a heterodimer consisting of a 31 and a 29 kDa subunit and RPrAII is a homodimer consisting of single 30 kDa subunits.

Studies on *Robinia pseudoacacia* lectins have generated some confusion concerning the precise molecular weight, and subunit composition of the individual lectins. Wantyghem et al (1986) identified two lectins in seeds, RPA 1 a dimer and RPA 3 a tetramer. However, in the same year Fleischmann et al (1986) described the isolation of two tetramer lectins terms RPA 1 and RPA 2 with similar subunit molecular weights. It appears therefore that the lectins exist as monomer, dimer, trimer and tetramer forms.

The present invention provides a diet and a dietary strategy to maximize the metabolic effects of lectin. In particular, soya fractions can be used such that the negative effects on the anti-nutritional fractions are reduced. Moreover, the beneficial effects of low doses of lectins can be used to enhance feed conversion of nutritionally poor soya fractions.

SUMMARY OF THE INVENTION

The invention provides a method for the control of mucosal cell proliferation in an individual in need thereof, comprising administering to an individual an effective amount of a lectin.

For all methods of the invention an individual can be any animal, preferably a mammal, more preferably a human.

The method may be for the control of gut lesions and/or mucositis. Control may be required where damage has been caused, in particular by a cell-damaging agent. The damage may be caused to cells and/or tissues. Damage may be caused to mammalian, in particular human cells and/or tissues.

The method is particularly useful for control of mucosal cell proliferation wherein the cell and/or tissue are one or more selected from the group consisting of those mucosal coverings of the gut, the mouth, the nasal passage, the oesophagus, the stomach, the small intestine, the large intestine (including the colon), epithelial tissue (eg covering the eye) and other mucosal cells and tissues.

The present invention also provides methods for the reduction and/or treatment of damage caused by a cell-damaging agent in an individual in need thereof, comprising administering to an individual an effective amount of a lectin. Particular and preferred features according to the first method described above, also relate to the method for reduction and/or treatment of damage caused by a cell-damaging agent.

In addition to the particular cell types described above, the reduction and/or treatment of damage caused by a cell-damaging agent according to the invention, relates to cells and tissues of the bone marrow, spleen, all blood generating cells, blood tissues, thymus, hair-producing tissue, eye tissue and testicular prostate tissue.

For the two methods described above, the cell-damaging agent includes radiotherapy, a chemotherapeutic agent or a combination thereof. Examples of radiotherapy, include, X-ray, gamma ray, proton source, neutron source, $\alpha$-emitter, and $\beta$-emitter. Examples of chemotherapeutic agents include 5-fluorouracil, Cisplatin, doxorubicin, methotrexate and taxol.

While not being limited to particular lectins, those preferred for the present method include lectin from kidney beam, soya bean, Jack bean, black locust (*Robinia pseudoacacia*) wheat germ, lotus seed, onion, lentil, tomato, potato or from a combination of two or more thereof.

The methods described above, may be advantageously used when the lectin is in combination with a cytoprotectant. Examples of groups of cytoprotectants and specific examples are given in the detailed description of the invention.

The present invention also provides a method for the reduction and/or treatment of a metabolic disorder. Examples of suitable metabolic disorders include obesity or an obesity related disorder, cardiovascular, stroke, gastrointestinal or related conditions and control of mucosal cell proliferation.

All preferred features of the first two methods of the invention, also apply to the third.

It is also an object of the invention to provide a composition which comprises a lectin and a cytoprotectant. Such compositions may be for simultaneous, separate or sequential use in the prevention or treatment of damage caused by a cell-damaging agent. Preferably the lectin is purified or isolated.

For the above described methods and compositions, the lectin is preferably administered in a concentration of a 0.3 g to 0.1 µg per kg body weight per day, preferably 1 mg to 0.15 µg per kg body weight per day.

It is a further object of the invention to provide a diet, comprising, lectin, consumed for a period of from 2 to 5 days. This diet is advantageously followed by a period of up to 7 days of a high quality diet.

A further object of the invention is a cyclic diet comprising at least 2 cycles of a diet described above.

All diets according to the invention preferably comprise a lectin both in a concentration of from 0.2 g to 0.05 g per kg body weight per day.

A diet according to the present invention may be used in combination with radiotherapy and/or chemotherapy. In particular it may be used for, during or after the administration of the cell-damaging agent.

A further object of the invention is the use of soya waste products, optionally including the soya waste faction in any aspect according to the invention.

BRIEF DESCRIPTION OF THE DRAWINGS

FIG. 2 shows growth of rats fed on soya albumin diet followed by lactalbumin diet in repeated cycles in comparison with that of rats pair fed on control diet throughout the experiment. Times of switching the rats to different diets and food intakes are also indicated.

FIG. 6 shows the predicted amino acid sequences of lectin cDNA clones from *Robinia pseudoacacia* bark.

FIG. 7 shows the predicted amino acid sequences of lectin cDNA clones from *Robinia pseudoacacia* seed.

DETAILED DESCRIPTION OF THE INVENTION

Figure 1B:
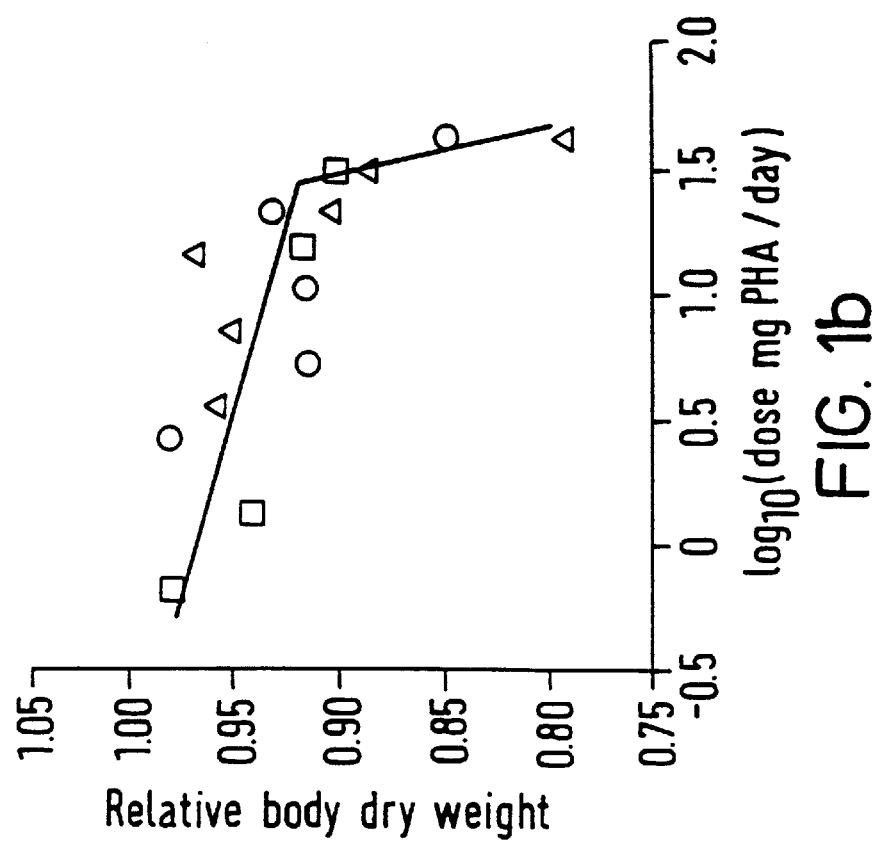
FIG. 1 shows dry body weights of rats fed diets containing different amounts of phytohaemagglutinin for 10 days (Experiments 1 a,b,c).
FIG. 1a; body dry weight vs mg PHA/day and FIG. 1b relative body dry weight vs. log10 (mg PHA/day). (o, Experiment 1a; Experiment 1b; Δ Experiment 1c).

The present text discusses the invention as a number of aspects. All preferred features of each and all aspects relate to each other and in particular to the methods and other objects according to the present invention.

Accordingly, the present invention provides, as a first aspect, the use of a lectin in the manufacture of a medicament for the control of mucosal cell proliferation. The control of mucosal cell proliferation includes the reduction and/or treatment of any damage to mucosal cells and/or tissues. Throughout this text, "reduction" means any effect which mitigates any damage or any medical disorders, to any extent, and includes prevention. Throughout this text, "treatment" means any amelioration of disorder, disease, syndrome, condition, pain or a combination or two or more thereof.

In particular, the first aspect of the invention pertains to the control of mucosal cell proliferation in the reduction and/or treatment of mucositis and/or gut lesions.

Control of mucosal cell proliferation is particularly useful in the reduction and/or treatment of damage caused by a cell-damaging agent. Typical cell damaging agents of all aspects of the present invention include radiotherapy, chemotherapy or a combination thereof. In the present application the terms "irradiation+ and "radiotherapy" are used as having the same meaning, which is a source of irradiation which may, or may not be applied as a therapeutic technique.

The first aspect of the present invention is particularly effective in the control of mucosal cell proliferation prior to, during or following radiotherapy, chemotherapy or a combination thereof. The invention is achieved as a result of the protective and repair capabilities of lectins.

Mucosal cells are those which make up any mucous membrane (the moist membrane lining many tubular structures and cavities). Many are those which provide a protective layer between the external environment and the internal organs of an animal. Mucosal cells/tissue include cells of the nasal sinuses, the respiratory tract, the gastrointestinal tract as well as biliary and pancreatic systems. The surface of the mouth is also lined by a mucous membrane. The mucous membrane consists of a surface layer of epithelium, which contains glands secreting mucous, with underlying layers of connective tissue and muscularis mucosae, which forms the inner boundary of the mucous membrane.

The use of the lectin for the control of mucosal cell proliferation is particularly useful in relation to cells of the gastrointestinal tract. The control may be for an increase in functional and/or length of the gastrointestinal tract or for control of the nature and/or density of gastrointestinal-cell expressed surface glycoproteins. Other uses in relation to control of mucosa cell proliferation include the reduction and/or treatment of bowel disorders such as inflammatory bowel disease and irritable bowel syndrome as well as the reduction and/or treatment of gut lesions, and the repair and replacement of mucosa cells prior to, during or following, radiotherapy, chemotherapy or a combination of two or more thereof.

The applications of these control features includes:
(a) Gut cell proliferation leading to an increase in functional gut area and length which could be a useful therapy where gut function is impaired as for instance via surgery or accident, and or
(b) Control of gut cell turnover rates which may allow control over the nature and density of expressed surface glycoconjugates as these become progressively more complex as cells age. As the glycoconjugates affect certain gut properties, such as propensity to bacterial attachment, lectin administration could be envisaged as a therapeutic or prophylactic control for these properties.

In particular, the control of cell proliferation may be used for obtaining an increased nutrient capacity of the small intestine and/or controlling cell gut expression of glycoconjugates. Such effects are not necessarily medical disorders and may be only cosmetic or functional, above and beyond the satisfactory medical level.

These effects may also be useful for the *Robinia pseudoacacia* lectin use in reduction and/or treatment of a metabolic disorder.

According to a second aspect of the invention, there is provided the use of a lectin in the manufacture of a medicament for the reduction and/or treatment of damage caused by a cell-damaging agent. Cell-damaging agents include radiotherapy, chemotherapy or a combination thereof. Damage includes gut lesions and/or mucositis, in particular.

For the first and second aspects of the invention, sources of radiotherapy include, but are not limited to, X-ray, gamma ray, proton or neutron sources, α or β emitters or a combination of two or more thereof. The radiotherapy may be used in combination with chemotherapy using a cytotoxic agent such as methotrexate, Cisplatin and/or 5-fluorouracil, and also in combination with surgical procedures.

For the first and second aspects of the invention, chemotherapeutic agents include any cytotoxic agent and include, but are not limited to agents such as 5-fluorouracil, Cisplatin, doxorubicin, methotrexate, a taxol or a combination of two or more thereof. As described above, one or more chemotherapeutic agent can be used in combination with radiotherapy and/or surgical procedures.

The invention is of particular applicability to the reduction and/or treatment of damage to mammalian tissue, more particularly human tissue. The present invention is of particular importance to human tissue because of the considerable requirement for radiotherapy and/or chemotherapy in the treatment of cancer. However, the present invention is also applicable to the veterinary industry, including farm animals and pets.

The first aspect of the invention relates to all mucosal cells and/or tissues, and includes mucosal cells and tissues within a whole body as well as outside of a whole body, including isolated mucosal cells and tissues. The second aspect of the invention relates to all biological matter, including whole bodies and parts thereof, and includes isolated organs and isolated tissue, including mucosal cells and tissues. The invention also relates to matter which is subjected, intentionally or unintentionally, to any cell-damaging agent.

The invention is of particular use to biological mater which is particularly sensitive to cell-damaging agents such as radiotherapy and/or chemotherapeutic agents. Such biological matter according to the first aspect of the invention includes the mucosal coverings of the gut, the mouth, the nasal passage, the oesophagus, the stomach, the lung, the small intestine, the large intestine (including the colon and the rectum), epithelial tissue (eg covering the eye) as well as any other mucosal cell and/or tissue. Such biological matter according to the second aspect to the invention includes all of the mucosal cells and tissues defined above, as well as bone marrow, spleen, all blood generating cells, blood tissue, thymus, hair-producing tissue, eye tissue and testicular/prostate tissue. The sensitivity of the gut to damage by a cell-damaging agents is linked to its metabolic status. It is the growth factor effect of lectins, in particular on the gut (and especially the small intestine) which is understood to be important in the prophylactic and/or therapeutic affects prior to and during administration of cell-damaging agents.

Lectins can be classified as either "toxin" or "non-toxic". Toxic lectins include or are classified as type 2 Ribosome Inactivating Proteins (RIPs). These are hybrid molecules which contain a toxic (A) subunit which, after entering the cell, irreversibly inhibits protein synthesis and a lectin subunit (B) which facilitates the entry of RIP into the cell. Type 2 RIPs such as Ricin are some of the most poisonous substances known to man with potential $LD_{50}$ values as low as 0.1 g per kg body weight, they can irreversibly damage a mammal on long term administration, ultimately leading to death.

The binding of lectins to cells varies greatly. Some bind weakly and for others the binding is very strong. "Strongly binding" describes a lectin wherein if 10 mg is administered orally to a rat, over 75% (and up to 100%) of the lectin binds to the gut. Kidney bean lectin is an example of a strongly binding lectin. In some instances strong binding may lead to toxicity and these lectins may be referred to as toxic.

The lectins of the present invention include those in either in naturally occurring compositions or purified therefrom (or any extent), chemically synthesised lectins, modified lectins or derivatives (naturally occurring or synthetic) thereof. Derivatives of lectins include one or more subunits of multi-subunit lectins. Methods are well known in the art for the production of lectins and include, the purification of lectins from natural sources (Pusztai and Palmer, 1977: Carvalho, 1993) and biotechnology-derived lectins such as described in U.S. Pat. No. 4,889,842. The lectins according to the invention are preferably functional equivalents to "originally" isolated *Robinia pseudoacacia* lectins. The functionality of any *Rubinia pseudoacacia* lectin can be determined in accordance with its ability to attach to specific glycoconjugate structures. Most preferably, a polypeptide is a *Robinia pseudoacacia* lectin according to the present invention if it is an equivalent, i.e. 40%, preferably 50%, preferably 60%, more preferably 70%, even more preferably, 80% or more identical at the amino acid level or DNA sequence level to any known *Robinia pseudoacacia* lectin.

Any lectin can be used according to the first aspect of the invention. Many lectins are known. A widely used method for characterising lectins is their carbohydrate binding specificity. A number of the carbohydrate binding specific groups include: N-acetyl-D-galctosame, -D-mannose, -L-fucose, beta-lactose, Galactosyl-beta-(1-3)-N-acetyl-D-galactosamine, D-glucose, N-acetyl-glucosamine, N-acetyl-neuraminic acid. Some lectins fall within more than one carbohydrate binding specific group. Of particular interest for the present invention are lectins from; kidney bean, soya bean, Jack bean, black locust, wheat germ, lotus seed, onion, lentil, tomato, potato and combinations of two or more thereof.

Since lectins are proteins, they are clearly subject to destabilisation/denaturation by a number of parameters such as heat, acid, alkali etc. Some lectins are more resistant to these effects than others. Since the use of lectins in the present invention (throughout) requires their protein properties it is important that the lectins are not completely destroyed or denaturated prior to or during their use (eg in the strong acid conditions of the stomach and the mild alkali conditions of the lower gut). Accordingly, lectins for use in the present invention may need to be first characterised with regard to how they may be affected during processing and/or administration. Such characterisation is standard technology and can be conducted easily by any person skilled in the art. The concentration of lectin required for any of the aspects of the invention will vary if the lectin has been denatured or destabilised in any way.

The concentrations of lectins which have been provided in this text are based on their natural properties with effectively no reduction of their activity by denaturation or destabilisation. Thus, the concentrations of lectins which are provided are not absolute but reflect the activity of the lectin. Accordingly, a composition, for example, which has a lectin whose activity has been reduced by half, but which is present in double the concentration is the same as a composition which has half the quantity of lectin but where the activity of the lectin has not been altered. Furthermore, the activity of any lectin may be increased by modification, for example during recombinant production and/or by producing truncated mutants which have increased activity. The same considerations as to the concentration verses activity of lectin also applies to lectins with increased activity. All modified lectins are covered by the present invention, including those with increased or decreased activities, and include, for example, truncated lectin monomers with full or modified activity. All modified *Robinia pseudoacacia* lectins or derivatives thereof are covered by the present invention, including those with increased or decreased activities, and include, for example, truncated lectin subunits and/or differently glycosylated versions with full or modified activity. Also included are protein sequences which include one or more of the critical amino acids involved in biological activity of any lectin (preferably all of those amino acids and all of the biological activity). For example, the active region(s) of RPA polypeptide b sequence are described in Nishiguchi et al, 1997, and include the following; (amino acid: position); aspartate: 87, phenylalanine: 130, threonine: 215, leucine: 217, serine: 218.

The *Robinia pseudoacacia* lectin according to the invention may be form, or is an equivalent to a lectin from any part of the *Robinia pseudoacacia* plant, preferably bark, seed, root, leaf, root nodule, phloem or wood or a combination of two or more thereof. In accordance with the present invention, the *Robinia pseudoacacia* lectin may comprise only one polypeptide subunit. The polypeptide subunit may be any of those known in the art (e.g. RPbAI (a or b), RPbAII(c), RPsAI or RPsAII, RprAI or RPrAII) or an equivalent thereto, or is a polypeptide subunit not yet identified. Preferably, the *Robinia pseudoacacia* lectin of the first aspect of the invention comprises a monomer, a dimer, a trimer or a tetramer of subunits, or a combination of two or more thereof. This enables mimicking of polypeptide groupings as they occur in nature. The monomer, dimer, trimer, tetramer may be of the same, or more than one type of polymer subunit. The tetramer preferably comprises four bark polypeptide a subunits, four bark polypeptide b subunits or an intermediate mixture of a and b subunits. The lectin polypeptides may correspond to one or more of the amino acid sequences as set out in FIG. 6 or FIG. 7, preferably at least 80% identical thereto.

The lectins according to the present invention are tissue protectants.

Preferably the lectin is purified to a level of from 80 to 100%. In this text, the term "purified" means substantially without impurities. *Robinia pseudoacacia* lectin at these levels of purity is preferred for use in pharmaceutical compositions and use in medicine. The *Robinia pseudoacacia* lectin is preferably purified to a level of 90%, or above, most preferably 95% or above. Preferred features of the first aspect of the invention, as described above, also apply to the second aspect of the invention.

The first and second aspects of the invention relate to the manufacture of medicaments, the particular dosage regime for which will ultimately be determined by the attending physician and will take into consideration such factors as the lectin or lectins being used, animal type, age, weight, severity of symptoms and/or severity of treatment being or to be applied, method of administration of the composition, adverse reactions and/or other contraindications. Specific defined dosage ranges can be determined by standard designed clinical trials with patient progress and recovery being fully monitored. Such trials may use an escalating dose design using a low percentage of the maximum tolerated dose in animals as the starting dose in man. Preliminary guidance for dosage ranges can be taken from the results given in the experimental section of this text and by the following ranges which have been extrapolated to humans.

An appropriate upper limit appears to be a concentration of a lectin up to approximately 0.3 g per kg body weight per day. A concentration of 0.3 g per kg body weight per day may well produce an upset gastro-intestinal tract in a patient but these symptoms may be acceptable on the basis that the patient has an increase chance of survival from diseases such as cancer. An appropriate lower limit appear to be a concentration of lectin around 0.0001 mg (0.1 $\mu$g) per kg body weight per day. Preferred intermediate dosage concentrations include the presence of a lectin up to approximately 0.2 g, 0.15 g and 0.05 g per kg body weight per day, and thereafter of concentrations approximately 1 mg, 0.5 mg, 0.1 mg, 0.01 mg and 0.005 mg per kg body weight per day. With regard to concentrations of lectins for administration, when not used for a therapeutic or prophylactic effect the dose of lectin may be slightly raised.

The medicaments for all aspects of the present invention can be used to provide the required concentration of lectin in one or more "intake" per day ("intake" including any form of administration). Some aspects of the invention may suit a single intake of a high lectin concentration, whereas others may suit a number of intakes, evenly or unevenly spaced over the same period, but with a lower lectin concentration per intake.

Use of the lectin in the manufacture of any medicament according to the present invention may be in combination with a suitable pharmaceutical carrier and/or excipient. Such carriers and excipients are well known in the art (eg Handbook of Pharmaceutical Excipients (1994) 2nd Edition, Eds. A. Wade/P. J. Weller, The Pharmaceutical Press, American Pharmaceutical Association). Of particular use according to the present invention are compositions and/or medicaments which are formulated in a colonic drug delivery system or in a capsule. Suitable excipients include pharmaceutical grade starch, gelatin, oil, sugar, alcohol or water (preferably sterile). The composition may be a mixed preparation for administration, or may be a combined preparation for simultaneous, separate or sequential use (or administration). In a combined preparation, the lectin and any other components may be separate and may be administered in any order. The lectin may be purified according to the second aspect of the invention. Features and preferred features of the first and second aspects of the invention also apply to the third.

The first and second aspects of the invention also cover the use of a lectin in combination with a cytoprotectant. The cytoprotectant is preferably a radiosensitiser, a chemoprotectant (including free-range scavengers), a growth factor or a combination of two or more thereof. From the above list of cytoprotectants the following examples are preferred: radiosensitisers—vitamin K mimetics such as Synkavit or Menadione, gadolinium texaphyrin or iobenguane (([[3-iodo-13311)phenyl]methyl]guanidine): chemoprotectants—Sulcraphate, cysteine, cysteamine, Ethyol, Balazipone or dosmalfate; free radical scavengers—WR 3689 (2-[[3-methylamino)propyl]amino]ethanediol dihydrogen phosphate ester, AD 20 (2-[[2-methoxyphenyl)acetyl]amino]-2-propenoic acid or nitroxide antioxidant; growth factors—granulocyte colony-stimulating factor (G-CSF), granulocyte-macrophage colony-stimulating factor (GM-CSF), Erythropoietin (EPO), epidermal growth factor (EGF), keratinocyte growth factor (KGF), transforming growth factor (TGF $\alpha$ and $\beta$); any interleuking including IL-11 and IL-15, insulin-like growth factor (IGF), nerve growth factor (NGF), platelet derived growth factor (PDGR), Bombesin, Relaxin, Calcitonin, colostrum-derived growth factor (CDGF), amlexanox or amoxanox, protegrin, pilocarpine hydrochloride, stem cell factor (STF), thrombopoietin, steel factor (SF), any interferon, including interferon or any cytokine.

In addition to cytoprotectants, the medicament may include one or more other pharmaceutical compounds/agents. In particular, anti-microbial agents may be included. Such agents may be included to fight secondary infections, for example secondary infections associated with mucositis, inflammatory bowel disease, irritable bowel syndrome, etc.

The medicament manufactured according to any aspect of the invention is preferably administered by mouth or rectally (for ease of route to one or more parts of the alimentary canal) although parenteral administration of the medicament may also be used.

A third aspect of the invention provides the use of a lectin in the manufacture of a medicament for the reduction and/or treatment of a metabolic disorder. Also included according to the third aspect of the invention is the use of a lectin in the manufacture of a medicament for attaining loss/ reduction of weight. Such weight loss/reduction is not necessarily related to a medical condition (eg metabolic disorder) and may be a purely cosmetic weight loss/ reduction. The lectin may be any lectin according to the invention, most advantageously derived from soya bean, kidney bean or black locust (details given above according to the first or second aspects of the invention).

Metabolic disorders include any disorder which is related to and/or a result of the metabolism of the body, in particular obesity and obesity related disorders such as hyperglycaemia (type II diabetes), cardiovascular, stroke, gastro-intestinal and gastro-intestinal related conditions. A metabolic disorder may require the control of mucosal cell proliferation, or the control of mucosal cell proliferation may be independent of a metabolic disorder.

All relevant features of the first and second aspects of the invention also apply to the third.

The higher the concentration of lectin, the faster may be the prevention or the treatment of the metabolic disorder. However various factors may influence the preferred concentration of lectin dosage, as is discussed herein.

According to a fourth aspect of the invention, there is provided a composition comprising a lectin, for use in the control of mucosal cell proliferation, the reduction and/or treatment of damage caused by a cell-damaging agent, the reduction and/or treatment of a metabolic disorder, or a combination of two or more thereof. This aspect of the invention applies, in particular for lectins which have not previously been known to have a medical use. Relevant features of the first, second and third aspects of the invention also relate to the fourth aspect of the invention.

According to a fifth aspect of the invention there is a composition, comprising a lectin and a cytoprotectant. Such an aspect of the invention may relate to the first and/or second aspect of the invention, since it may be one embodiment of a medicament manufactured according to the first or second aspect of the invention. Accordingly, relevant features of the first and second aspects of the invention described above, also apply to the fifth aspect of the invention. A particularly preferred composition is one where the lectin is at least partially purified or isolated, as described above under first and second aspects of the invention.

The composition of the fifth aspect of the invention may be a mixed preparation for administration, or may be a combined preparation for simultaneous, separate or sequential use (or administration). In the combined preparation, either the lectin or the cytoprotectant part of the composition may be administered first.

The fifth aspect of the invention is particularly suitable for use in the reduction or treatment of damage caused by a cell-damaging agent, in particular, irradiation and/or chemotherapy. Accordingly, it may be appropriate to include in the composition pharmaceutically acceptable excipients and/or carriers as described according to the first and second aspects of the invention. As also described according to the first and second aspects of the invention, the composition is most effective against the biological matter which is most sensitive to cell-damaging agents, in particular, irradiation and chemotherapy.

All relevant features of aspects one to four of the present invention also apply to the fifth aspect.

A sixth aspect of the invention applies to a method for the manufacture of a composition according to the fifth aspect of the invention. The method may comprise admixing the lectin and the cytoprotectant, optionally in combination with one or more ingredients, such as additional cytoprotectants, anti-microbial agents and/or pharmaceutically acceptable excipients and/or carriers. Alternatively, for a composition which has the different components administered simultaneously, separately or sequentially, the individual components are prepared which may be in combination with other ingredients, including pharmaceutically acceptable excipients and/or carriers.

A seventh aspect of the invention provides a method for the control of mucosal cell proliferation according to the first aspect of the invention, the reduction and/or treatment of damage caused by a cell-damaging agent according to the second aspect of the invention and for the reduction and/or treatment of a metabolic disorder (including related features) according to the third aspect of the invention. Any method according to this aspect of the invention is preferably administered to an individual in need thereof. Relevant features aspects one to six, also apply to the seventh aspect of the invention. The method preferably comprises the intake of a total dietary concentration of lectin of up to 0.3 g, more preferably 0.2 g, per kg body weight per day. The metabolic disorder may be any of those described above. The lectin may also be any of those described above, preferably derived from soya bean, kidney bean or black locust.

According to a eighth aspect of the invention there is provided a diet comprising a lectin for a period of 2 to 5 days, or for an indefinite (long-term) duration. Relevant features of aspects one to seven of the invention, also apply to the eighth aspect. The lectin may be any of those described above according to the first aspect of the invention, more preferably a lectin derived from soya bean, soya whey or black locust.

The diet according to the eighth aspect of the invention preferably comprises a total lectin content of up to 0.3 g, preferably 0.2 g per kg body weight per day. Also provided is a dietary supplement which brings the total dietary intake of lectin to a concentration of 0.3 g, preferably 0.2 g per kg body weight per day. The lectin may be any one, or a combination of two or more lectins described above according to the first aspect of the invention. Preferably the lectin of the diet is derived from soya beans, kidney beans or black locust. Such a diet and/or dietary supplement is useful in the control of mucosal cell proliferation according to the first aspect of the invention, for the reduction and/or treatment of damage caused by a cell-damaging agent according to the second aspect of the invention, for the reduction and/or treatment of a metabolic disorder according to the third aspect of the invention or a combination of two or more thereof. The diet and/or dietary supplement may also contribute towards non-medically related weight loss/reduction.

The diet and/or dietary supplement applies to any animal, including humans.

The diet according to the eighth aspect of the invention is particularly useful when followed by a period during which a high quality diet is administered. A high quality diet, according to the present invention can be defined as a diet which provides all of the essential proteins, fats, carbohydrates, minerals and vitamins necessary for the normal growth of an animal. The essential components of the high quality diet are preferably in an optimal ratio. A high quality diet should not contain any component which would slow or inhibit the growth and development of the animal. A preferred feature of a high quality diet is that there is a positive conversion of food eaten into body weight.

The high quality diet preferably follows on immediately or shortly after (up to 2 days) the lectin diet according to the eighth aspect of the invention. The high quality diet is most useful for a period of up to 7 days, advantageously for a period of up to 5 days. The diet may also be advantageous for use in the long term (greater than one month, preferably greater than one year) treatment of metabolic disorders and cosmetic weight loss.

When used in combination with a cell-damaging agent (although not necessarily at the same time of administration), the lectin feeding part of the diet is best restricted to a period of up to 5 days because 48–72 hours is often sufficient to complete a full cycle of intestinal turnover and to hereby obtain the benefits of high nutrient absorption and utilisation rates in the control feeding part of the cycle. The high quality feeding part of the cycle is best restricted to about 5 days to obtain maximum improvements in feed conversion efficiency.

Preferably, the diet which comprises a period of feeding with a lectin, followed by a period of feeding with a high quality diet is repeated at least twice to form a cyclic diet. The cycles may be repeated up to 20 times, preferably up to 10 times, most preferably up to 6 times.

The cyclic diet described provides transient increases in nutrient uptake efficiency which are mediated by lectin administration. Therefore, by cycling of lectin-containing and lectin-free diets, enhancement of nutritionally dependent situations can be engineered. For example, with appropriate dietary timing an athlete can optimise performances for major events.

The diet according to the eighth aspect of the invention is particularly useful prior to or after a method of treatment by irradiation and/or chemotherapy. In such situations, the diet may be even more effective when used in combination with a cytoprotectant, such as those described for the first and second aspects of the invention.

According to an ninth aspect of the invention, there is provided the use of soya waste products, including the soya whey fraction in any aspect or related aspect of the invention. The use of such soya waste products reduces the requirement for the removal of lectins from soya products before being used as a foodstuff and efficiently utilises low value soya waste products.

A further aspect of the invention provides a method to produce each of the previous aspects of the invention as described above. Production of the purified lectin involves either the isolation and purification of the one or more lectin (eg from a plant or tissue culture) or to the synthetic production (eg by recombinant technology). Production of a composition comprising a lectin involves combining the lectin with any one or more ingredients for the composition. Production of the diet and/or dietary supplement involves obtaining one or more lectin and optionally combining with any one or more ingredients for a diet and/or dietary supplement.

For all aspects, objects, methods etc of the present invention, the most preferred lectin is believed to be from black locust.

The present invention also relates to a composition, comprising a lectin (alone or in combination with another lectin) and a pharmaceutically acceptable excipient. This particular aspect of the invention is particularly relevant for a lectin or a group of two or more lectins which are not previously known to have been included in such a composition, eg the lectin from black locust).

With regard to concentrations of lectins given herein, any of these can be used as a upper limit and/or a low limit, thus providing a variety of useful ranges of concentration.

For all therapeutic (alone) aspects of the invention (ie where the lectin is used only after any treatment, cell-damaging agent source etc), the preferred dose of lectin is less than 0.2 g per kg body weight per day.

The present invention will now be illustrated by a number of non-limiting examples. The examples refer to the accompanying drawings.

EXAMPLES

Materials and Methods

Purification of PHA

For the obesity and chemotherapy examples, PHA was purified by affinity chromatography on Sepharose 4B-fetuin using the method of Pusztai & Palmer (1977) with some improvements (Carvalho, 1993). Kidney beans were extracted with 0.05M sodium borate buffer (pH 8.0) and separated into globulins and albumins by dialysis against 0.033M sodium acetate buffer, pH 5.0. E-type PHA (erythroagglutinating) fractions were adsorbed on to Sepharose 4B-fetuin at pH 7.6 (0.05M Tris-HCl) and desorption with 0.5M glycine-HCl buffer, pH 3.0 also containing 0.5M NaCl, followed by dialysis and freeze-drying. For the purification of L-type (lymphoagglutinating) PHA, after the removal of small amounts of E-type PHA from the albumins by Sepharose 4B-fetuin, the non-adsorbed fraction was fractionated on a sulphopropyl cation exchange HPLC column (TSK SP-5PW, 21.5 mm×150 mm; Anachem GB Ltd) in 0.005 M sodium acetate-acetic acid buffer, pH 3.8 containing 0.1M NaCl and eluated by a programmed increasing ionic strength gradient (0.1–0.5M NaCl). Finally, lower molecular weight impurities were removed by chromatography on Sephadex G-100, and pure L-type PHA was recovered after dialysis and freeze drying. Recovery: 0.32 g and 0.61 g E-type and L-type PHA respectively per 100 g kidney bean meal.

For the radiotherapy example, PHA was isolated by grinding 50 g of kidney beans in a grinder with a sieve of pore size 1 mm. 500 ml of 0.02M acetic acid containing 0.1 g ascorbic acid was added and stirred for 30 minutes at room temperature. The pH was adjusted to 5.0 with 1M NaOH and the solution stirred for a further 2 hours at room temperature. The solution was allowed to stand at 4° C. overnight and was then centrifuged at 9000 rpm for 15 minutes. 0.075 g $CaCl_2$ was added to the supernatant and the pH adjusted to 9.0 with 1M NaOH. The supernatant was allowed to stand again overnight at 4° C. and the sample was spun at 3000 rpm for 10 minutes. The sample was then dialysed against Tris (pH 7.6) before purification on a Fetuin-Sepharose 4B affinity column. The PHA peak was eluted with a 0.05M glycine buffer and then the PHA fraction was dialysed against water before freeze drying.

Insulin assay

Immunoreactive plasma insulin concentrations were measured using a double-antibody precipitation technique (MacRae et al., 1991) and a rat insulin standard (Incstar Corporation, Stillwater, Min. USA). $^{125}$I-labelled bovine insulin, 5 μCi/0.1 μg (ref. IM38) was supplied by Amersham International plc (Amersham, Bucks.) and antiserum to porcine insulin raised in guinea pigs by Miles Scientific (Stoke Poges, Slough). Anti-guinea pig IgG serum and normal guinea pig serum were from the Scottish Antibody Production Unit (Law Hospital, Carluke, Lanarkshire).

Plasma glucose

Concentration of glucose in plasma samples were carried out by the autoanalyzer method of Trinder (1967).

Antibody production

Antibodies to KTI, BBI, LA were developed in rabbits according to the method of Harboe and Inglid (1973) as described before (Hajos et al., 1995). Antibody to SBA was obtained from Sigma Chemical Co (UK Ltd).

Competitive indirect ELISA

Indirect ELISA assays were used for the quantitative determination of SBA in gut samples (Hajos et al., 1995). However, with LA the ELISA plates were coated with LA and the immune-complex was formed by using a rabbit anti-LA IgG-type antibody. Results were expressed as per cent material recovered of the dose incubated intragastrically.

Electrophoretic separation of antinutrients in gut samples

SDS gel electrophoresis, followed by semi-dry transblotting on to nitrocellulose membranes and immunostaining with antigen-specific antibodies to the antinutrients were carried out as before (Hajos et al., 1995).

Composition of experimental diets

TABLE 1

Composition of diets for obesity and chemotheraphy examples.

|  | Lactalbumin (LA) | Kidney Bean (KB) | KB Albumins (KBA) |
|---|---|---|---|
| Maize starch | 373 | 177 | 372 |
| Potato starch | 100 | 100 | 100 |
| Glucose | 150 | 150 | 150 |
| Corn oil | 150 | 150 | 150 |
| Vitamin mix | 50 | 50 | 50 |
| Mineral mix | 50 | 50 | 50 |
| Lactalbumin | 127 | 63 | 102 |
| Kidney bean meal | — | 260 | — |
| Kidney bean albumin | — | — | 26 |
| L-methionine | — | 2.1 | 0.9 |
| L-tryptophan | — | 0.25 | 0.13 |
| Silicic acid | 0.4 | 0.4 | 0.4 |

All components are given as g constituent/kg diet. For composition of vitamin and mineral mixes see Carvalho (1993).

TABLE 2

Composition of diets for soybean anti-nutrient examples

| Diet | 1. Control | 2. Soya albumins (SBALB) |
|---|---|---|
| Lactalbumin | 120 | 0 |
| Soyabean albumins | 0 | 110 |
| Maize starch | 380 | 390 |
| Potato starch | 100 | 100 |
| Glucose | 150 | 150 |
| Corn oil | 150 | 150 |
| Vitamins | 50 | 50 |
| Minerals | 50 | 50 |
| L-tryptophan | 0 | 0.3 |
| L-methionine | 0 | 1.2 |
| L-phenylalanine | 0 | 1.0 |
| L-leucine | 0 | 2.3 |
| L-isoleucine | 0 | 2.6 |
| L-valine | 0 | 2.6 |
| Silicic acid | 0.4 | 0.4 |

All components are given as g constituent/kg diet. For composition of vitamin and mineral mixes see Grant et al. (1993).

TABLE 3

Composition of diets for radiotherapy examples

| Diet | 10% Lactalbumin | PHA (bean protein) |
|---|---|---|
| Lactalbumin | 120 | 90 |
| Kidney bean | 0 | 127.5 |
| Maize starch | 379.6 | 280.9 |
| Potato starch | 100 | 100 |
| Glucose | 150 | 150 |
| Corn oil | 150 | 150 |
| Vitamins | 50 | 50 |
| Minerals | 50 | 50 |
| L-tryptophan | 0 | 0.14 |
| L-methionine | 0 | 1.07 |
| Silicic acid | 0.40 | 0.40 |

All dietary components are given in g/kg diet. The PHA content of kidney bean is 2.6%. Accordingly, with a restricted daily dietary intake of 6 g, the input of PHA/mouse was 20 mg. Composition of vitamin mixture: Thiamine, 1000 mg; Pyridoxine (B6), 1000 mg; Riboflavin, 100 mg; p-amino benzoic acid, 1000 mg; Nicotinic acid, 3000 mg; Ca Pantothenate, 2000 mg; Folic acid, 500 mg; Biotin, 550 mg; Inositol, 40,000 mg; α-tocopherol, 25 g; Retinyl acetate, 1150 mg; Calciferol ($D_3$), 1500 mg; Vitamin $B_{12}$, 2.5 mg; Menadione, 500 mg; Choline chloride, 100 g; Maize starch, 5000 g.

Administration of 5-FU 300 mg of 5-fluorouracil was stirred in 14 ml of distilled water. 1M NaOH was added slowly until the 5-FU had dissolved. The solution was made up to a final volume of 20 ml. The final pH of the solution was 8.3. A dose of 150 mg/kg body weight was administered to the animal by intraperitoneal injection. Immediately after the injection, the rats were offered 15 g of the control diet and food was available ad-libitum for the remainder of the experiment.

Irradiation source

Cobalt $^{60}$Co gun; 6.75 Gy total, full body exposure; dose rate: 0.3 Gy/min.

Example 1

Three separate experiments (1a,b,c) were carried out to the same design. Rats weaned at 19 days were maintained on stock diet for 11 days and fed LA-diet for 3 days (Table 1) to reach 82–84 g starting weight. The rats were then selected into groups of five rats according to body weight and within each group they were allocated at random to treatment. Rats in each group were fed daily 6 g diet in the morning on a control, LA-diet or diets based on the LA-diet with different levels of PHA inclusion so that their daily PHA intake was between 0.65 and 42 mg/rat (0.007 and 0.45 g/kg body weight). After 10 days the rats were fed 2 g of respective diets in the morning and killed precisely 2 hours later. Gastrocnemius muscles were excised and rinsed and both bodies and muscles were freeze-dried and weighed. In Experiment 1c bodies were ground to a powder and extracted with chloroform-methanol (2:1; v/v) for lipid determination.

Figure 1A:
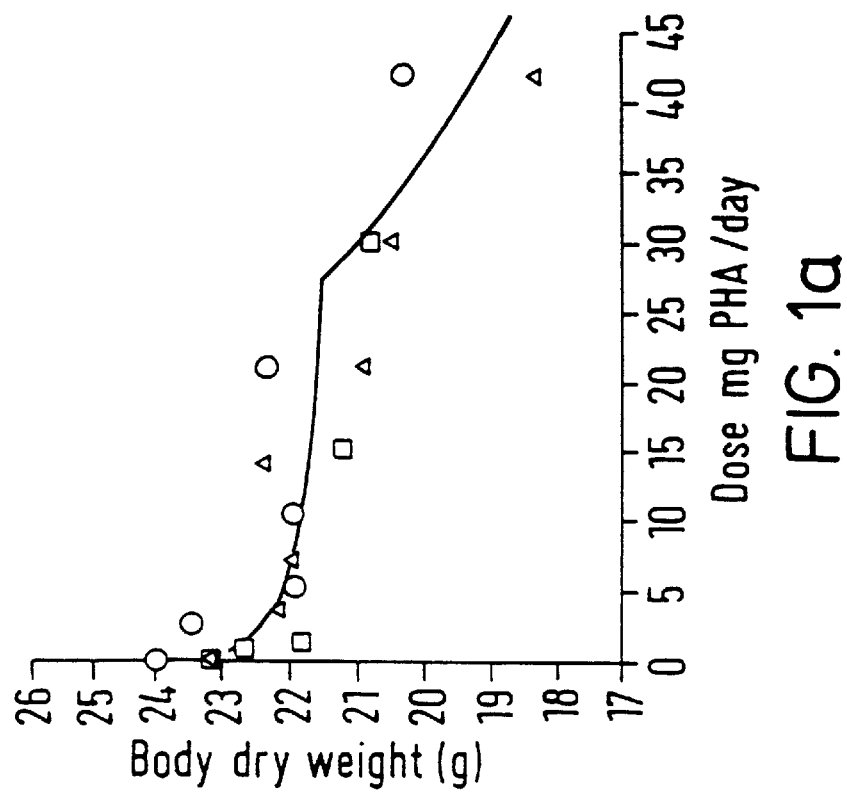

The mean body weights for the control groups in Experiments 1a,b,c were very similar lying between 23.2 and 24 g. Feeding rats with diets containing PHA in the range of 0 to 42 mg/rat/day (0 to 0.45 g/kg body weight) reduced their body weight in a biphasic manner (FIG. 1a,b; Table 4, 5). There was a small reduction in body weight even at low levels of PHA (e.g. 4% at 3.5 mg/rat/d; 0.04 g/kg body weight) after which relatively large increases in the lectin dose (to about 0.32 g/kg) produced only modest further reductions in the body weight. Thus, averaged over all the experiments at doses below 10 mg PHA/d (0.12 g/kg body weight) the mean body weight reduction was 1.14 (se 0.25) g when compared to control (4.9% of control body weight). At daily doses of PHA between 10 and 27 mg (0.12 and 0.32 g/kg body weight) there was a further reduction of 0.64 (se 0.21) g (2.7% of control body weight). However, at higher doses (0.20–0.45 g/kg body weight) the reduction became more appreciable. The relationship between relative body dry weight (as proportion of zero dose control), RBDW, and the PHA dose expressed as mg/d from three separate feeding trials (Experiments 1a,b,c) below PHA dose of 27 mg/d was:

$$RBDW=0.918 \ (se \ 0.008)-0.0334 \ (se \ 0.0062) \times log10 \ (dose \ PHA/27)$$

Above this PHA dose the equation was:

$$RBDW=0.918 \ (se \ 0.008)-0.5138 \ (se \ 0.0876) \times log10 \ (dose \ PHA/27)$$

Changes in the dry weight of the gastrocnemius (skeletal) muscles followed a similar trend with increasing lectin input (Table 4, 5). The proportional loss of muscle weight compared to control rats tended to be about 1.5–2.0 times that of the equivalent loss of body weight (Table 4, 5), but at daily doses of less than 10 mg PHA (0.12 g/kg body weight) the difference between the proportional loss of body and muscle weights was not significant (p>0.05).

Similar to the reduction in body and muscle weights, the lipid content of the body of rats was reduced by increasing the dose of PHA in the diet (Table 5; Experiment 1c). However, proportionally the lipid loss exceeded that of both the body and skeletal muscle although the ratio of the losses remained roughly constant for all doses.

TABLE 4

Body weights and gastrocnemius muscle weights of rats fed diets containing different levels of PHA for 10 days.

| Dose of PHA mg/rat/day | Body dry weight (BDW) g | (% loss vs control) | Gastrocnemius dry weight g | (% loss vs control) |
|---|---|---|---|---|
| Experiment 1a | | | | |
| 0 | 24.0 | — | 0.184 | — |
| 2.6 | 23.5 | 2.2 | 0.183 | 0.7 |
| 5.2 | 21.9 | 8.7 | 0.166 | 9.7 |
| 10.5 | 22.0 | 8.5 | 0.155 | 15.5 |
| 21.0 | 22.4 | 7.0 | 0.153 | 16.5 |
| 42.0 | 20.4 | 15.2 | 0.129 | 29.8 |
| SED | 0.61 | | 0.0074 | |
| Experiment 1b | | | | |
| 0 | 23.2 | — | 0.178 | — |
| 0.6 | 22.7 | 2.3 | 0.174 | 2.1 |
| 1.3 | 21.8 | 6.0 | 0.161 | 9.4 |
| 15.0 | 21.2 | 8.4 | 0.151 | 15.3 |
| 30.0 | 20.9 | 10.0 | 0.143 | 19.9 |
| SED | 0.35 | | 0.0039 | |

All doses were tested by 5 rats per group

TABLE 5

Body composition of rats fed diets containing different levels of PHA for 10 days (Experiment 1c).

| PHA dose mg/rat/d | 0 | 3.5 | 7 | 14 | 21 | 30 | 42 | SED |
|---|---|---|---|---|---|---|---|---|
| Body dry weight (g) | 23.2 | 22.2 | 22 | 22.4 | 21 | 20.6 | 18.4 | 0.47 |
| (% loss vs control) | — | 4.3 | 5.2 | 3.4 | 9.5 | 11.2 | 20.7 | |
| Gastrocnemius dry weight (g) | 0.196 | 0.188 | 0.184 | 0.185 | 0.167 | 0.154 | 0.134 | 0.0061 |
| (% loss vs control) | — | 4.1 | 6.1 | 5.6 | 14.8 | 21.4 | 31.6 | |
| Lipid weight (g) | 4.18 | 3.9 | 3.86 | 3.56 | 3.39 | 2.82 | 2.25 | 0.17 |
| (% loss vs control) | — | 6.7 | 7.7 | 14.8 | 18.9 | 32.5 | 46.1 | |
| Total Muscle dry weight* (g) | 9.27 | 8.89 | 8.7 | 8.75 | 7.9 | 7.28 | 6.39 | |
| Other dry weight** (g) | 9.75 | 10.39 | 9.46 | 10.14 | 9.69 | 10.46 | 9.75 | |
| Ratio % loss of gastrocnemius vs % loss of lipid | — | 0.61 | 0.79 | 0.38 | 0.79 | 0.66 | 0.69 | |

Footnotes to Table 5.
All groups had 5 rats per group.
*TMDW was estimated based on assumptions (i) gastrocnemius dry weight/TMDW is same for all treatments and (ii) TMDW/BDW = 0.4 for the control group.
**OW was calculated by subtracting the sum of LW and TMSW from the total weight.

PHA is widely regarded as a nutritional toxin because rats fed exclusively on kidney bean proteins containing high levels of PHA (0.8–1.0 g/kg body weight) die within a few days (Pusztai, 1991). However, as PHA is not harmful for germ-free rats its toxic effects in rats with a conventional microflora are likely to be the consequence of the dramatic E. coli overgrowth in the small intestinal lumen which was negligible below 0.2 g/kg but rose sharply and in proportion with the increase in the level of PHA in the diet (Pusztai et al., 1993). Example 1 shows that in this low concentration range where no bacterial overgrowth occurs (below 0.2 g/kg), the anti-nutritive effects of PHA are slight in rats harbouring a conventional microflora as the reduction in body weight is minimal after 10 days exposure to the lectin. Moreover, in contrast to muscle atrophy observed at high doses (0.45 g/kg and above), reduction in skeletal muscle weights below PHA doses of 0.10 g/kg body weight was slight and proportional to loss in final body weight (Tables 4, 5). However, relative to the control, the proportional loss of lipid was higher than the proportional loss of muscle although the ratio between them remained roughly constant (Tables 4, 5). Thus the first effect of the lectin is a stimulation of body lipid catabolism and thus a low dose of lectin may be a suitable treatment for metabolic disorders such as obesity.

Example 2

In Examples 2–5 the insulin response of rats to PHA was tested. In Example 2, rats were fed diets containing 42 mg PHA/day and blood insulin levels were measured after 9 and 10 days, respectively. Individually housed male Hooded Lister spf (specific pathogen-free) rats weaned at 19 days were maintained on stock diet (Special Diet Services, Manea, Cambridgeshire) for about 14 days ad lib, followed by restricted feeding (8 g/rat/d) for 5 days on a control, lactalbumin-based diet (LA; Table 1). Rats were fed three times daily; 2.5 g at 09.00 am, 1.0 g at 13.00 pm and 4.5 g at 18.00 pm. On the fifth day, the rats were given 1.5 g LA diet between 9.00 and 9.30 am and pre-experimental blood samples were taken from the tail vein 2 h later. Blood was collected in heparinized tubes (25 µl heparin solution containing 26 USP units/tube) and centrifuged in a bench-top centrifuge at +1° C. for 15 min. Plastic granules were used to aid the separation of plasma from erythrocytes; it was divided into 100 µl aliquots and stored at −2020 C. until assayed. The rats were then randomly divided into two groups of 13 animals and individually housed. Group 1 was fed exclusively on a diet containing kidney bean (KB-diet; Table 1) for 10 days (8 g diet/rat/day; divided into 3 meals: 2.5 g at 09.00 am, 1 g at 13.00 pm and 4.5 g at 18.00 pm) while the control group was pair-fed on LA diet under the same conditions. On the 9th day, blood samples were taken in the morning exactly 2 h after the morning feed of 1.5 g of KB-diet and this protocol was repeated on the 10th (last) day. The rats were then killed under ether anaesthesia, the abdomen cut open and the rest of their blood was collected from the heart. The gastrointestional tract together with the pancreas was removed and after a quick rinse with ice-cold water, they were frozen in liquid nitrogen. Control rats were treated the same way except that they were given 1.5 g LA-diet before the blood samples were taken. Plasma samples were kept frozen till assayed for insulin.

Insulin was extracted from the pancreas (six randomly selected rats of each group) after homogenisation of a sample of this tissue (about 25–50 mg of dry weight) with 10 ml of acidified ethanol (ethanol:water:conc. $H_2SO_4$= 96:18:2.5; v/v/v) overnight in a cold room and then centrifuged at 1,500 g for 10 min in the cold. The clear supernatant was diluted to about 1:200 (v/v) with insulin assay buffer before including them in the insulin radioimmunoassay.

Feeding rats with KB containing 42 mg PHA/rat/day (0.45 g/kg body weight) for 10 days significantly reduced the plasma insulin concentration from the pre-experimental level of 2.97 (sd 0.84) ng/ml to 0.36 (sd 0.05) on the 9th day of the experiment (Table 6). The depression was apparently permanent during PHA exposure because blood samples taken on the 10th day were similarly low, 0.23 (sd 0.06) ng insulin/ml. In contrast, the plasma insulin levels in controls remained high, 3.31 (sd 0.30) and 1.55 (sd 0.21) ng/ml on the 9th and 10th days of the feeding respectively.

TABLE 6

Weight and insulin content of pancreas of rats fed with diets containing kidney beans or lactalbumin (control) for 10 days.

|  | Pancreas Dry Weight | | Insulin | |
|---|---|---|---|---|
|  | (mg) | (mg/100 g body weight) | µg/pancreas | µg/g protein |
| KB | 162 ± 20* | 982 ± 122* | 22.38 ± 7.63* | 182 ± 80* |
| LA | 138 ± 16 | 605 ± 63 | 40.60 ± 12.71 | 354 ± 152 |

KB = Kidney Bean Diet
LA = Lactalbumin Diet

Values are means±SD for 6 animals in each group. *Significantly different from Lactalbumin-fed controls (P<0.01).

The absolute and relative dry weights of the pancreas of rats fed on KB-diet at the highest dose of PHA for 10 days were significantly increased in comparison with pair-fed controls (Table 6). In contrast, the insulin content of the pancreas expressed either as µg/pancreas or µg/g protein was significantly decreased. Despite the highly significant reduction in insulin levels, plasma glucose concentrations were not significantly altered in KB-fed animals with an overall mean value of 1.7 (sd 0.1) mg glucose/ml for both treated and control rats.

The previously suggested link between the strong catabolic effects of high doses of PHA on body metabolism of lipids, carbohydrates and proteins and its lowering of plasma insulin levels (Pusztai, 1991) has now been confirmed. In fact, insulin levels were depressed not only in the blood circulation during the 10 day oral exposure of rats to PHA but also the insulin content of the pancreas was significantly reduced in these animals.

Example 3

Rats were weaned at 19 days, kept in groups of 8–10 rats and fed on stock diet for 12 days. They were then randomly selected into two groups (13 rats in each group), individually housed for the rest of the experiment and fed on stock diet for another 8 days. Rats, after fasting overnight, were given 2 g stock diet in the morning and 2 h later blood-sampled (pre-experimental sample). Immediately after this the rats were intragastrically incubated with a 1 ml extract of KB (50 mg; 5–7 mg PHA) while the controls were dosed with 1 ml 0.01 M phosphate buffered saline (0.9% NaCl; w/v; PBS). Blood samples were obtained from each animal at 15, 60 and 120 min after the incubation. A single dose of a soluble KB protein sample caused a gradual decrease in plasma insulin. The pre-experimental value of 1.78 (sd 0.22) ng insulin/ml plasma decreased to 1.05 (sd 0.22) ng/ml after 120 min, i.e. some 59% of the initial value (Table 7). In control rats the insulin level remained roughly constant within experimental errors at all time points [1.76 (sd 0.42) ng/ml].

TABLE 7

Relative insulin levels (expressed as % of control) in rats after acute intragastric exposure to kidney bean proteins or purified E-type or L-type lectins

| Time | Control | Kidney bean protein | E-type | L-type |
|---|---|---|---|---|
| 15 | 109 (36) | 82 (34) | 76 (27)* | 98 (32) |
| 60 | 97 (36) | 65 (21)* | 58 (23)* | 86 (34) |
| 120 | 89 (28) | 59 (15)* | 80 (39) | 81 (32) |

The results are means±SD and * indicates that the mean is significantly different 100 (p<0.05).

Example 4

Example 4 was conducted in the same manner as example 3 except that the test animals were gavaged with a 1 ml solution of either 5 mg E-type or L-type lectins. Some of these lectin samples were labelled with $^{125}I$ (total counts of 2,5–3 million cpm). The controls received PBS. Blood samples were taken at 0, 15, 60 and 120 min as before. To measure the actual amounts of PHA delivered into the duodenum, radioactivity was measured in both stomach and small intestinal washes in some rats killed 1 or 2 h after incubation.

In rats incubated with pure E-type PHA, the pre-experimental plasma insulin levels were also decreased in the first 60 min to 1.03 (sd 0.32) ng/ml in a similar way to that found in animals gavaged with KB proteins (Table 7). However, there appeared to be a slight recovery in the next 60 min which rendered the change in insulin level at 120 min not significantly different (p>0.05) from the pre-experimental value. A single dose of L-type PHA also appeared to cause a gradual reduction in plasma insulin but the changes were not significant at any of the time points during the 120 min of the experiment (1.39 sd 0.35 ng/ml at 120 min). The rates of stomach emptying in rats intubated with the lectins were slow and not significantly different for the two types of PHA (p>0.05). With E-type about 52% of the initial dose reached the small intestine after 120 min, while with L-type PHA this was slightly more, about 63%. Plasma glucose levels were slightly reduced on acute exposure to PHA and/or KB albumins from 1.6 (sd 0.2) to 1.4 (sd 0.2) mg/ml but the reduction was not significant (p>0.05).

A diet containing either pure E- or L-type PHA was able to exert a reduction in serum insulin as was seen with a diet containing kidney bean protein. Thus, the effect of reduced serum insulin is due to a direct effect of PHA and not due to the poor nutritional quality of the bean protein.

Example 5

Sixteen rats weaned at 19 days and housed individually during the experiment were fed stock diet for 15 days, followed by 5 days on LA-diet (8 g diet/rat/day). Twelve randomly selected rats were then switched to a diet containing kidney bean albumin (KBA-diet; Table 1) for the next 3 days, with a daily intake of about 30 mg PHA/rat, while four control rats continued with the LA-diet. In the evening of the 3rd day, instead of the evening meal, the rats on KBA-diet were intragastrically intubated with a 1 ml solution of 100 mg of KBA sample containing 25 mg PHA, while the controls were given the evening portion of their LA-diet. After this the animals were not fed again till the following morning when they were all given 2 g LA-diet to boost their plasma insulin level. Exactly 2 hours later the rats were blood-sampled (pre-experimental sample), those which had been pre-fed on KBA were randomly selected into groups of four and were gavaged with 1 ml solutions of either 20 mg KBA, or 5 mg E-type or 5 mg L-type PHA lectins some of which were $^{125}$I-labelled. The four control rats were gavaged with KBA (40 mg; 4–6 mg PHA) for comparison. Rats were blood sampled at 120 min, killed and pancreas removed and frozen for insulin assays.

Intragastric incubation with a single dose of purified PHA isolectins of rats pre-fed with diets containing KB albumin proteins or control diet and intubated with doses of PHA for 3 days substantially reduced the concentration of plasma insulin in the circulation. With both E-type and L-type lectins the difference in insulin levels between pre-experimental [0.59 (sd 0.05) ng/ml] and 120 min values [(0.15 (sd 0.09) ng/ml] was significant (p>0.05). Pre-feeding also appeared to speed up the rate of stomach emptying of intragastrically administered E-type lectins as over 80% of the dose reached the duodenum in the first 60 min. In contrast, L-type lectins were still slow to reach the duodenum and after the first 60 min about 50% of the initial amount of the PHA remained in the stomach. Despite the differences in the absolute plasma insulin concentrations between rats pre-fed on KBA-diet (low) and those kept on a control diet (moderately high), after gavaging with KB albumin proteins the proportional decrease in plasma insulin was similar in both groups of rats. The insulin content of the pancreas was slightly but not significantly reduced after the 3 days pre-feeding with KBA-diet from 58.3 (sd 10.8) in controls to 42.5 (sd 8.3) (g insulin/pancreas). However, there were no significant changes in the pre-experimental mean plasma glucose levels of about 1.6 (sd 0.2) mg/ml, although the values decreased slightly during the experiment. There were no significant changes in body and muscle weights after exposure to PHA for 3 days.

Example 6

Dietary strategy for overcoming the antinutritional effects of soya by exploiting the increase in feed conversion efficiency after short periodic exposures of rats to soya whey having a high agglutinin content.

Male Hooded-Lister rats were weaned at 19 days and given free access to stock diet (Labsure, Manea, U.K.) for 7 days after which they were fed an LA control diet (100 g lactalbumin protein/kg; Table 2) ad libitum for 3 days, followed by feeding 6 g of the same diet/rat/d for 5 days. Water was freely available at all times. The rats were then divided into 2 groups, 5 rats in each group. The diet for the experimental group contained 100 g/kg protein based on SBALB (Table 2). The control group of rats were fed LA diet throughout the experiment and its amount was restricted to the voluntary intake of the test rats. The experimental design was such (FIG. 2) that initially the soya group was fed soya diet for 7 days, switched to LA diet for 8 days, followed by soya diet for 7 days and a 7 day LA diet period respectively. Next, after another 6 days on soya diet followed by 20 days on LA diet, the rats were finally exposed to soya diet for a 5 day period. On the following morning which was the 61st day of the combined feeding experiment, all rats were given 2 g LA diet after which the soya group was intragastrically incubated with 280 mg SBALB dissolved in 2 ml saline while the controls received saline only. Rats were killed by halothane overdose exactly 90 min later and fully dissected. Stomach and small intestine were removed and the latter was cut into 10 cm long sections. The lumen of each tissue was washed with 2 ml ice-cold distilled water, freeze-dried and later reconstituted with distilled water (1 mg dry matter/100 $\mu$l) and used for ELISA. A washed intestinal section of 2 cm (between 5–7 cm from the pylorus) was taken for histological examination. All tissues were freeze-dried and weighed. Rat bodies were also freeze-dried and used for the determination of protein and lipid contents. Stomach and small intestinal sections were homogenised (3 times) with 0.1 M D-galactose solution (5 ml/dry sample) and these extracts were used for ELISA. Throughout the experiment faeces were collected daily and used for nitrogen determinations.

In a control experiment the first cycle of the switching experiment was repeated but this time in addition to the SBALB group, a second set of test rats were first fed a diet containing LD-SBALB instead of SBALB for 7 days, followed by LA diet for 8 days while the control rats were pair-fed LA diet for the whole 15 days of the experiment. Weight gain, digestibility and feed conversion efficiency of the two test groups were compared with those of the control group in the two separate parts of the cycle.

The preparation used in the feeding experiment was shown by ELISA to contain 38.7 g SBA/kg. LD-SBALB contained less than 4 g SBA/kg LD-SBLAB. The weight of rats fed alternately on soya and LA diets was always significantly less at the end of each soya feeding period, including the last one, than that of the corresponding pair-fed control rats (Table 8 & 9). However, rats in the test group always grew faster in the LA diet period following soya feeding than control rats kept on LA diet throughout (FIG. 2; Table 9). Moreover, feed conversion efficiency of the test group in the LA period was always significantly higher than that of the controls (Table 9).

TABLE 8

Body weight (BW) and composition of rats

| Diet | Control | Test (SBALB) |
|---|---|---|
| Initial BW (g) | 88.8 ± 3.5[a] | 86.5 ± 2.1[a] |
| Final BW (g) | 283.5 ± 7.5[a] | 263.6 ± 7.2[b] |
| Dry BW (g) | 111.5 ± 3.0[a] | 104.6 ± 3.2[b] |
| Lipid (g) | 54.1 ± 4.5[a] | 51.8 ± 5.5[a] |
| Protein (g) | 45.7 ± 1.5[a] | 44.2 ± 2.1[a] |
| Lipid (g/kg Dry BW) | 485.2 ± 33.3[a] | 493.8 ± 36[a] |
| Protein (g/kg Dry BW) | 410.7 ± 19.9[a] | 402.1 ± 25.5[a] |

Results are given as means±SD of 5 rats per group. Values in a horizontal row with distinct superscripts differ significantly ($P \leq 0.05$).

TABLE 9

Weight changes and feed conversion efficiency of rats in test and control periods

| Treatment | Initial weight (g) | Final weight (g) | Feed conversion (g/g intake) |
|---|---|---|---|
| Test period Soya or LA diets | | | |
| Switch 1 1–7d | | | |
| Control | 88.8 ± 3.5[a] | 92.2 ± 1.0[a] | 0.08 ± 0.02[a] |
| Test | 86.6 ± 2.1[a] | 81.7 ± 3.2[b] | negative[b] |
| Switch 2 16–22d | | | |
| Control | 133 ± 3.0[a] | 137 ± 2.8[a] | 0.06 ± 0.04[a] |
| Test | 129 ± 3.0[a] | 120 ± 3.9[b] | negative[b] |
| Switch 3 30–35d | | | |
| Control | 168.5 ± 3.7[a] | 174 ± 4.0[a] | 0.11 ± 0.08[a] |
| Test | 163.5 ± 3.7[a] | 153 ± 5[b] | negative[b] |
| Switch 4 56–61d | | | |
| Control | 282.5 ± 6[a] | 283.5 ± 6[a] | 0.01 ± 0.08[a] |
| Test | 281.6 ± 5.1[a] | 263.6 ± 7.2[b] | negative[b] |
| Control period (LA diet) | | | |
| 8–15d | | | |
| Control | 92.2 ± 1[a] | 133 ± 3[a] | 0.43 ± 0.03[a] |
| Test | 81.7 ± 3.2[b] | 129 ± 3[a] | 0.49 ± 0.03[b] |
| 23–29d | | | |
| Control | 137 ± 2.8[a] | 168.5 ± 3.7[a] | 0.38 ± 0.04[a] |
| Test | 120 ± 3.9[b] | 163.5 ± 3.7[a] | 0.52 ± 0.04[b] |
| 36–55d | | | |
| Control | 174 ± 4[a] | 282.5 ± 7.5[a] | 0.36 ± 0.02[a] |
| Test | 153 ± 5[b] | 281.6 ± 5.1[a] | 0.43 ± 0.02[b] |

For each period values in a horizontal row with distinct superscripts differ significantly ($P \leq 0.05$).

In the soya feeding period the weight and nitrogen content of faeces of the test group was significantly higher than that of the control rats. However, in the LA periods there were no significant differences in these faecal values between rats in the test and control groups. Moreover, neither the lipid and protein contents nor their concentration in the rat bodies were significantly different in the two groups (Table 8).

Rats fed LD-SBALB in the test period gained more weight and had better feed conversion efficiency than those fed SBALB but their performance was still below that of rats fed LA diet (Table 10). However, rats switched from LD-SBALB to LA diet in the control period showed no significant improvement in feed conversion efficiency comparable to that with SBALB rats in the LA diet feeding part of the cycle (Table 10).

TABLE 10

Effect of lectin depletion on weight gain and feed conversion.

| Treatment | Initial weight (g) | Final weight (g) | Feed conversion (g/g intake) |
|---|---|---|---|
| Test period Soya or LA diets | | | |
| Control | 80.8 ± 1.5[a] | 86.8 ± 2.0[a] | 0.14 ± 0.03[a] |
| SBALB | 80.6 ± 1.1[a] | 78.7 ± 0.7[b] | negative[b] |
| LD-SBALB | 80.1 ± 1.1[a] | 83 ± 1.1[c] | 0.07 ± 0.03[c] |
| Control period (LA diet) | | | |
| Control | 86.8 ± 2[a] | 126.8 ± 2.5[a] | 0.42 ± 0.03[a] |
| SBALB | 78.7 ± 0.7[b] | 126.7 ± 2.7[a] | 0.50 ± 0.03[b] |
| LD-SBALB | 83.0 ± 1.1[c] | 124.2 ± 2.6[a] | 0.43 ± 0.03[a] |

For each period values in a horizontal row with distinct superscripts differ significantly ($P \leq 0.05$).

Effects on internal organs. The weights of stomach, small and large intestines, spleen, kidneys, thymus, lungs, heart and gastrocnemius muscles were not affected by feeding rats alternately with soya and LA diets for 61 days. However, the weight of the pancreas was significantly higher and that of the liver lower in the test group than in the controls.

In conclusion, diet-switching in which rats were fed alternately in short cycles on diets containing soya or lactalbumin has shown that it is possible to take advantage of the hyperplastic growth induced by SBA or other lectins to improve both absorption and utilisation of high-quality nutrients when the high-quality diet is fed. With this novel method processing of soya or other lectin-containing foodstuffs is not necessary and, moreover, soya waste products or other lectin-containing foodstuffs containing high amounts of lectin can be used (including in particular the whey fraction remaining after the removal of soya globulin proteins for many industrial uses).

Example 7

The ability of orally ingested PHA to protect rats from a high dose of chemotherapy, and in particular its tissue protectant effect on the gut was investigated.

For groups, each consisting of 5 rats were maintained on a precise dietary regime for a period of 7 days (Table 11).

TABLE 11

Chemotherapy dietary protocols

| Treatment | Dietary protocol |
|---|---|
| 1 | LA diet throughout, no 5-FU |
| 2 | LA 3d, inject 5-FU, LA 4d |
| 3 | PHA 3d, inject 5-FU, LA 4d |
| 4 | PHA 3d, inject 5-FU, PHA 3d, LA1d |

Key
LA = lactalbumin
PHA = *Phaseolus vulgaris* agglutinin
5-FU = 5-Fluorouracil Rats (approx 100 g) pre-dosed with PHA were offered 10 g of the control diet (Table 1) containing 10% lactalbumin.

Each animal was given the equivalent of 20 mg PHA in 0.9% saline by gavage. Rats were offered control diet in two feeds at 1000 & 1700 hours. The amount of food given was strictly paired to the amount of diet eaten by the PHA pre-dosed animals. If the animals were immediately post-dosed with PHA, the lectin was administered two hours post 5-FU injection by gavage. Animals neither pre- or post dosed with PHA were administered with 1 ml 0.9% saline by gavage. After 3 days, animals in three of the groups were administered a dose of 150 mg/kg body weight 5-FU. Body weight of each animal was recorded daily and the average body weight calculated.

Figure 3:
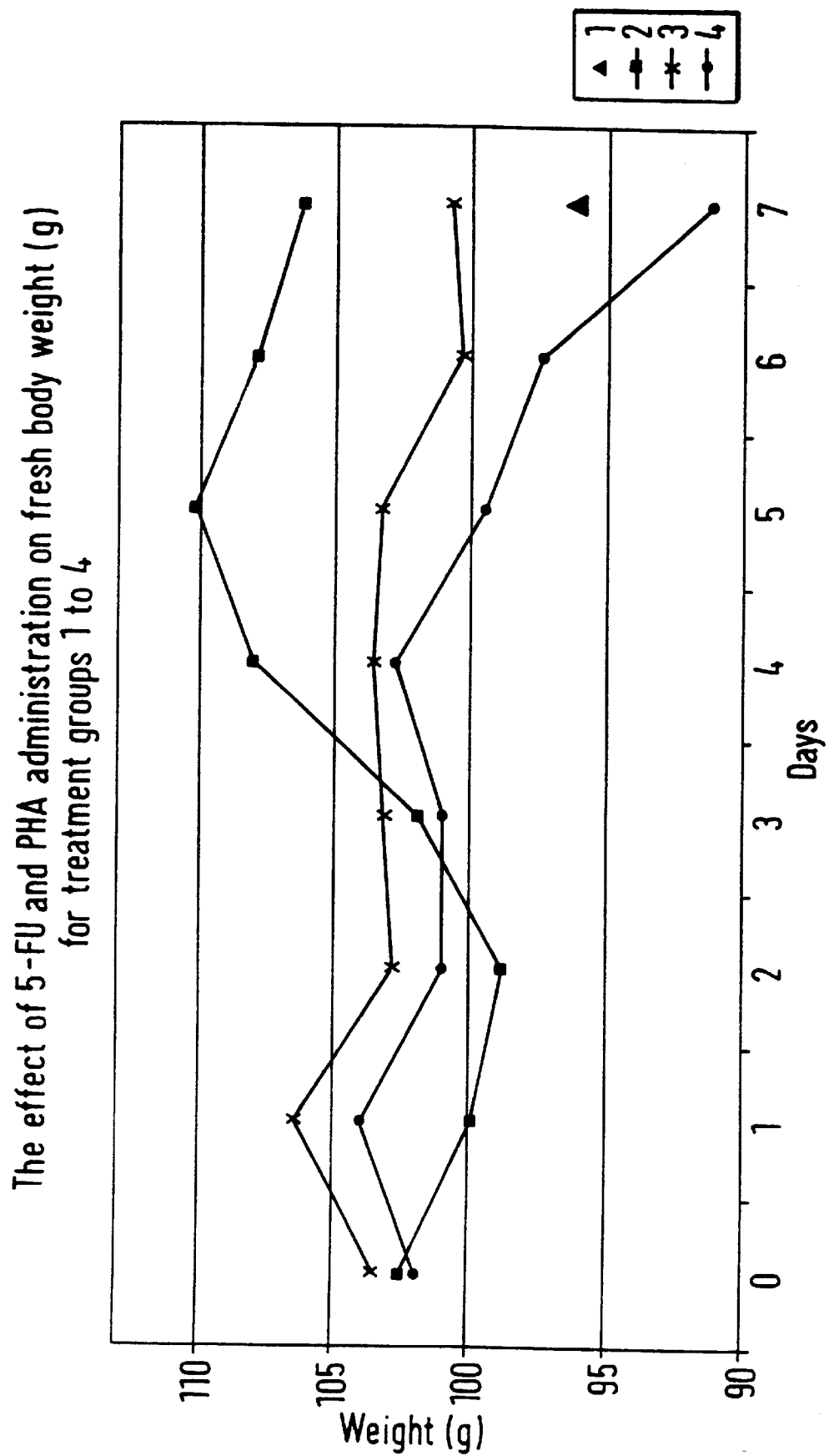
FIG. 3 shows the effect of 5-FU and PHA administration on fresh body weight

FIG. 3 (see also FIG. 3 data below) shows the effect of diet on animal body weight after administering 5-FU. Animals in the untreated control group grew at a steady rate throughout the experiment (data not shown). Animals maintained on the lactalbumin diet continued growing for 2 days after receiving the 5-FU diet before starting to lose weight. As this group was pair fed with the PHA pre-dosed group whose intake is reduced by the presence of PHA in the diet, when food was re-introduced ad lib there was a compensatory increase in their food intake before the full cytotoxic effect of 5-FU took hold. Animals pre-dosed on PHA for three days before receiving 5-FU and fed on lactalbumin containing diet afterwards maintained a stable weight for the following four days and appeared normal. In the remaining treatment, the animals showed a 5–10% weight loss four days after the 5-FU dose.

Figure data Appendix

Figure 3. The effect of 5-FU and PHA administration on fresh body weight (g).

| Treatment Group No. | Days | | | | | | | |
|---|---|---|---|---|---|---|---|---|
| | 0 | 1 | 2 | 3 | 4 | 5 | 6 | 7 |
| 1 | nd | nd | nd | nd | Nd | nd | nd | 96.2 |
| 2 | 102.5 | 99.9 | 98.8 | 101.9 | 108 | 110.2 | 107.9 | 106.2 |
| 3 | 103.5 | 106.4 | 102.8 | 103.2 | 103.6 | 103.3 | 100.3 | 100.7 |
| 4 | 101.9 | 104 | 101 | 101 | 102.76 | 99.5 | 97.4 | 91.2 |

Figure 4:
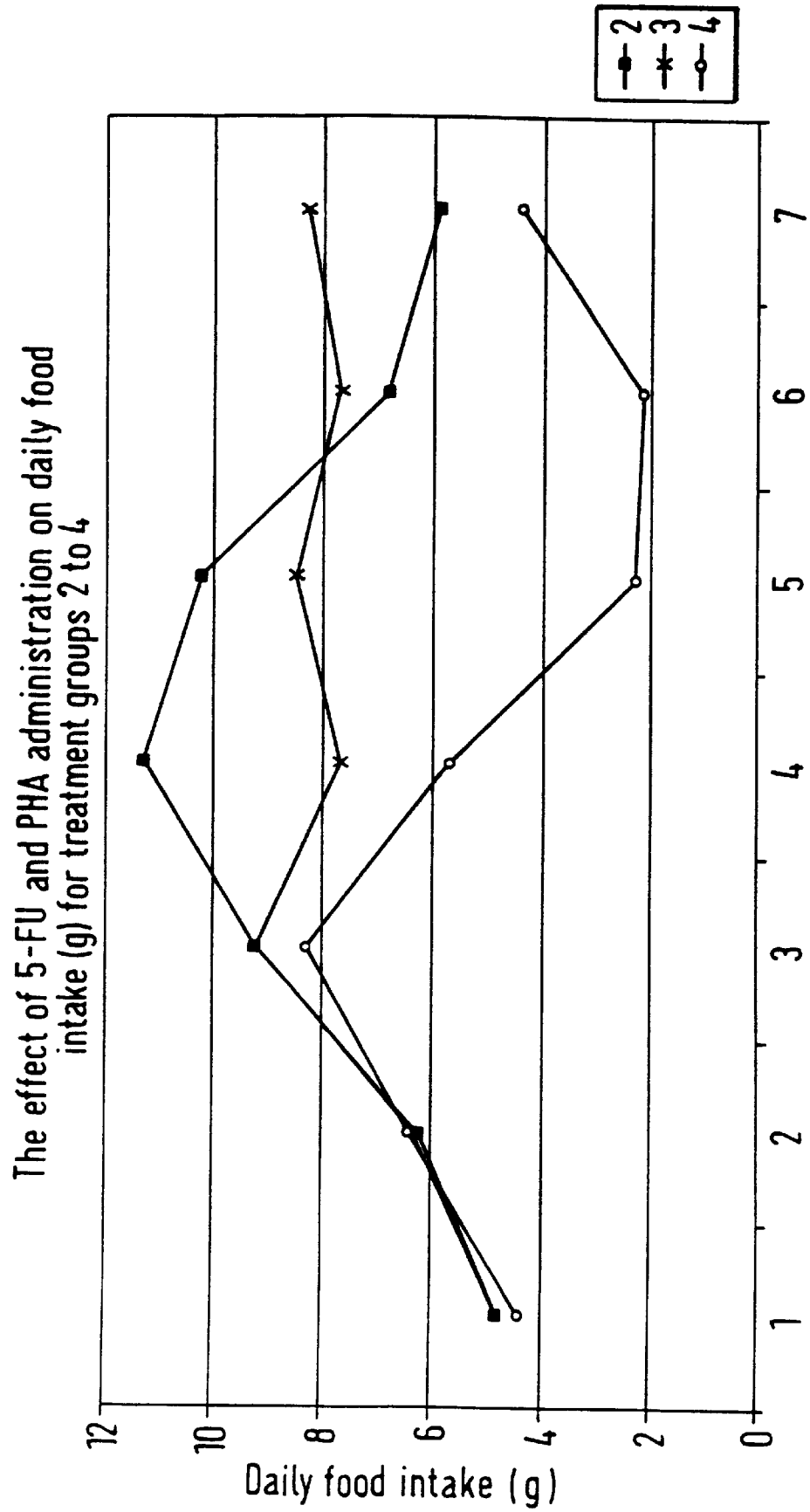
FIG. 4 shows the effect of 5-FU and PHA administration on daily food intake.

Figure 4. The effect of 5-FU and PHA administration on daily food intake (g).

| Treatment Group No. | Days | | | | | | |
|---|---|---|---|---|---|---|---|
| | 1 | 2 | 3 | 4 | 5 | 6 | 7 |
| 1 | nd | nd | nd | nd | nd | nd | nd |
| 2 | 4.8 | 6.22 | 9.22 | 11.3 | 10.4 | 6.8 | 5.9 |
| 3 | 4.8 | 6.3 | 9.2 | 7.7 | 8.5 | 7.7 | 8.3 |
| 4 | 4.42 | 6.4 | 8.3 | 5.7 | 2.28 | 2.14 | 4.4 |

TABLE 12

The average dry weights (mg) of the major organs of the gastrointestinal tract after 7 days.

| Treatment | Stomach | Small intestine | Jejunum | Ileum | Caecum | Colon |
|---|---|---|---|---|---|---|
| 1 | 141 ± 6 | 887 ± 28 | 185 ± 1 | 151 ± 8 | 124 ± 4 | 147 ± 6 |
| 2 | 140 ± 7 | 509 ± 55 | 90 ± 8 | 94 ± 11 | 99 ± 11 | 130 ± 11 |
| 3 | 136 ± 13 | 840 ± 253 | 189 ± 37 | 109 ± 24 | 114 ± 29 | 143 ± 24 |
| 4 | 125 ± 6 | 759 ± 318 | 168 ± 70 | 91 ± 24 | 93 ± 18 | 117 ± 21 |

Key
Treatments, see Table 11.

The food intake for each animal was recorded daily and the average food intake was calculated (FIG. 4 and FIG. 4 data below). In all treatments pre-dosed with PHA, the animals exhibited a steady increase in food intake prior to the 5-FU injection. Animals in the untreated control maintained a steadily increasing daily food intake (data not shown). Animals on the lactalbumin only diet reduced their food intake approximately one day after receiving the 5-FU dose. Animals pre-dosed on PHA for three days maintained a steady food intake at approximately 7 g/day for the four days following the 5-FU injection. The remaining treatment showed a large reduction in food intake for the four days following administration of 5-FU.

At the end of the experiment, the animals were sacrificed and then dissected. The dry weights of the major organs were recorded for each animal and the average weights calculated. The average dry weights of the major organs of the gastrointestinal tract for each treatment are presented in Table 12.

Key

Treatments, See Table 11.

The results show that administration of PHA before or after dosing with 5-FU had little effect on the stomach dry weight. However, PHA administration did have an effect on the small intestine dry weight. If only lactalbumin was included in the diet, the small intestine was damaged by 5-FU and the dry weight was reduced by almost 50%. If however, PHA was administered for 3 days either directly before (Treatment 3), or directly before and after dosing with PHA (Treatment 4), the lectin was able to protect the small intestine from damage by 5-FU and the dry weights were similar to that of the control.

Within the small intestine, both the jejunum and ileum tissue were the most susceptible to damage by 5-FU (Table 12). However, if PHA was administered either directly before, or before and after the 5-FU injection, the lectin was able to exert a significant tissue protectant effect, particularly to the jejunum. Pre-dosing the animals with PHA three days before the 5-FU dose also gave a significant protective effect to the whole small intestine (Table 12). Administering PHA either directly before (Treatment 3) or directly before and after dosing with 5-FU (Treatment 4) gave the best tissue protectant effect. This result suggests that the dose of PHA administered is able to stimulate growth and repair of viable cells in the small intestine and provide protection against the cytotoxic effects of 5-FU.

After 7 days, blood was collected from the animals and both the key molecular and cellular components were analysed. The results are presented in Table 13.

TABLE 13

Analysis of key molecular and cellular components of blood from control and treated animals

| Treatment | WBC no/mm$^3$ | RBC no/mm$^3$ | HGB g/100 ml | HCT g/100 ml | MCV $\mu$m$^3$ | MCH pg | MCHC g/100 ml | PLT no/mm$^3$ |
|---|---|---|---|---|---|---|---|---|
| 1 | 5.5 × 10$^3$ | 6 × 10$^3$ | 12.1 | 34.2 | 57.5 | 20.4 | 35.4 | 552 × 10$^3$ |
| 2 | 3 × 10$^3$ | 7.4 × 10$^3$ | 12.7 | 37.1 | 50.4 | 17.3 | 34.3 | 274 × 10$^3$ |
| 3 | 2.4 × 10$^3$ | 7.1 × 10$^3$ | 13 | 34.7 | 48.7 | 18.2 | 37.4 | 296 × 10$^3$ |
| 4 | 4 × 10$^3$ | 7.4 × 10$^3$ | 13 | 35.1 | 47.8 | 17.7 | 37.1 | 321 × 10$^3$ |

Key
Treatments as Table 3
WBC   White blood corpuscles
RBC   Red blood corpuscles
HGB   Haemoglobin
HCT   Haematocrit
MCV   Mean corpuscular volume
MCH   Mean corpuscular haemoglobin
MCHC  Mean corpuscular haemoglobin concentration
PLT   Platelets Following administration of 5-FU to rats fed the lactalbumin containing diet, the expected cytotoxicity was observed in both the number of white blood cells and platelets. None of the treatments had any significant effect on red blood cell count, haemoglobin & heamatocrit content, mean corpuscular volume or haemaglobin concentration when compared to the untreated control. Administration of PHA directly before the 5-FU dose (treatment 3) had little effect on the measured parameters when compared to the lactalbumin only treatment (Treatment 2). Administration of PHA before and after the dose (Treatment 4) increased the number of white blood cells produced relative to the lactalbumin control.

The above results suggest that the relative timing of administering an oral dose of a lectin in relation to the cytotoxic drug may affect the haematological toxicity of the drug.

Example 8

To identify a dose range which pre-dosing with PHA protected the gastrointestinal tract from damage by 5-FU.

3 groups of rats (5 rats per group) were fed on the standard diet (Table 1) and gavaged daily with either 200, 100 & 50 mg/kg/day PHA for 3 days. The food intake for each rat was recorded daily. A second set of 3 control groups of rats (5 rats per group) were fed on the standard diet and gavaged daily with 1 ml saline for 3 days. Each animal of the control group was pair fed to an animal in the PHA dosed groups. On the morning of the 4$^{th}$ day, each animal was injected with 150 mg/kg bodyweight 5-FU and then fed the standard diet for 6 days. 2 rats were fed on the standard diet ad libitum for 9 days. On the 9$^{th}$ day, the rats were killed and the animals dissected. After freezing in liquid nitrogen, the wet tissue weights were recorded.

TABLE 14

The effect of pre-dosing with 200, 100 or 50 mg/kg/day PHA for 3 days on the jejunum and ileum net weights (mg) after giving a dose of 150 mg/kg/BW 5-FU.

| Treatment | Jejunum (mg) | Ileum (mg) |
|---|---|---|
| Un-injected | 1006 | 909 |
| PHA 200 mg/kg/day | 1031 | 778 |
| Paired control 200 mg/kg/day | 848 | 753 |

TABLE 14-continued

The effect of pre-dosing with 200, 100 or 50 mg/kg/day PHA for 3 days on the jejunum and ileum net weights (mg) after giving a dose of 150 mg/kg/BW 5-FU.

| Treatment | Jejunum (mg) | Ileum (mg) |
|---|---|---|
| PHA 100 mg/kg/day | 984 | 800 |
| Paired control 100 mg/kg/day | 783 | 747 |
| PHA 50 mg/kg/day | 989 | 757 |
| Paired control 50 mg/kg/day | 761 | 722 |

By pre-dosing with 200 mg/kg/day PHA prior to injecting 5-FU, a significant protective effect was observed in the jejunum when compared to the un-injected treatment and paired control )Table 14). By reducing the dose of PHA to either 100 or 50 mg/kg/day, significant protection of the jejunum tissue was still observed when compared to the un-injected and pair control treatments. With the ileum tissue, PHA did not appear to exert such a profound tissue protectant effect for the doses examined when compared to the un-injected control. However, in every case, animals pre-dosed with PHA had larger ileal tissue than the corresponding pair fed controls.

The above examples demonstrate that chemotherapy can severely compromise the growth and viability of an animal. Manipulation of the diet, and in particular addition of a lectin before or after administering the cytotoxic drug can confer protection against chemotherapy. In particular, this protection is directed towards the viability and growth of the gastrointestinal tissues. The protection of gastrointestinal tissues after administering the cytotoxic drug was seen with doses of lectin of 200 mg/kg/day to 50 mg/kg/day.

Example 9

The ability of orally ingested PHA to protect mice from a lethal dose of irradiation, and in particular its tissue protectant effect on the gut was investigated.

Eight groups, each consisting of 12 albino male mice were each irradiated with 6.75 Gy irradiation (0.3 Gy/min). Each group of mice was maintained on a precise dietary regime for a period of 30 days (Table 15).

TABLE 15

Dietary protocols for the eight groups of mice used.

| Mouse Group no. | Dietary Regime | |
|---|---|---|
| Irradiated treatment groups | | |
| 1 | SD 2d LA 3d SD 11d | *ir* LA 14d |
| 2 | SD 2d LA 3d | *ir* PHA 7d LA 7d SD 11d |
| 3 | SD 2d LA 1.5d FT1.5d | *ir* PHA 7d LA 7d SD 11d |
| 4 | SD 2d LA 2d PHA.1d | *ir* PHA 7d LA 7d SD 11d |
| 5 | SD 2d PHA 3d | *ir* PHA 7d LA 7d SD 11d |
| Controls | | |
| 6 | SD 2d LA 3d | LA 14d SD 11d |
| 7 | SD 2d LA 2d | PHA 1d PHA 7d LA 7d SD 11d |
| 8 | SD 2d PHA 3d | PHA 7d LA 7d SD 11d |

Key to Table 15
SD Standard commercial diet (Charles River Ltd., Bioplan Ltd, Isaszeg, Hungary).
LA Lactalbumin diet. A semi-synthetic diet with known composition shown in Table 1 (lectin free) formulated in the laboratory. The lactalbumin was obtained from Sigma (Poole, Dorset).
PHA Kidney bean diet. A diet with known composition shown in Table 1 (containing the kidney bean lectin, PHA) formulated in the laboratory. The kidney bean source was cultivar 'Processor' (any other *Phaseolus vulgaris* bean-containing PHA is equally suitable).
FT Fasting (no diet).
*ir* Time of irradiation.

The number of mice surviving after 30 days, and their average body weight were recorded.

Figure 5:
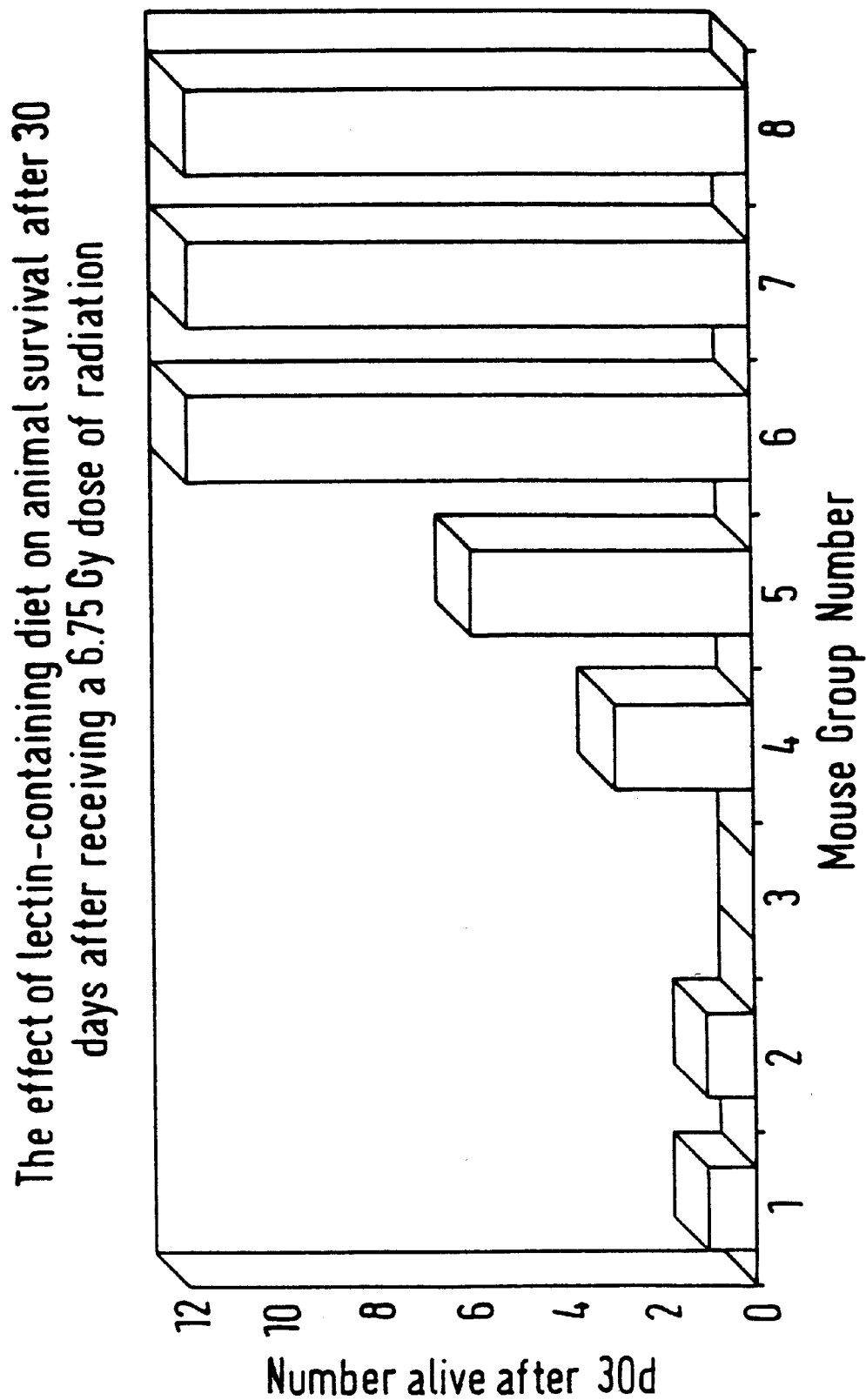
FIG. 5 shows the effect of lectin-containing diet on animal survival after 30 days, after receiving a 6.75 Gy dose of radiation.

FIG. 5 shows the effect of diet on animal survival after 30 days. Animals in the non-irradiated control treatments 6, 7 & 8 showed no effect of administering the standard commercial diet, lactalbumin diet and kidney bean diet on survival. No mortality was observed. Conversely, the animals in irradiated treatment groups 1, 2 & 3 with standard commercial, lactalbumin diets and the PHA diet administered after irradiation showed significant mortality (treatment 3 included a fasting period). Only a total of 2 animals in treatments 1–3 survived the irradiation treatment.

Where animals were fed on the PHA containing diet just before irradiation, (treatments 4 & 5) a significant increase in animals survival was observed. The number of surviving animals was closely correlated with the length of time animals were maintained on PHA diet directly prior to irradiation.

TABLE 16

The Average Body Weight of Animals after 30 days.

| Mouse Group No. | Average body weight (g +/− standard deviation) |
|---|---|
| 1 | 29.9 |
| 2 | 29.6 |
| 3 | — |
| 4 | 23.0 +/− 5.63 |
| 5 | 30.12 +/− 1.83 |
| 6 | 31.88 +/− 2.02 |
| 7 | 31.18 +/− 1.46 |
| 8 | 31.03 +/− 2.11 |

After 30 days, animals in the control treatments 6–8 weighed 30–32 g (Table 16). The animals in treatments 1–3 show high mortality. However, the animals in treatment groups 4 & 5 showed an increase in body weight correlated with the time animals were fed on the PHA containing diet prior to irradiation. In treatment group 5 (3 days on PHA containing diet prior to irradiation), the average body weight was similar to that of the control treatments. Administration of PHA into the diet at the dose studied had no detrimental effect. Where the lectin was administered before irradiation, a significant protective effect of PHA was observed.

Following irradiation of the animals, the average wet weights of small intestine, spleen and testicle were determined for each treatment (Table 17). Average weights for treatment group 7 were not determined.

TABLE 17

Small intestine, spleen and testicle weights (mg ± standard deviation) of surviving mice.

| Mouse Group No. | Small intestine | Spleen | Testicle |
|---|---|---|---|
| 1 | 999.8 | 72.5 | 49.4 |
| 2 | 1335.2 | 176.5 | 62.0 |
| 3 | — | — | — |
| 4 | 1032.0 ± 266.7 | 105.2 ± 25.7 | 53.6 ± 1.6 |
| 5 | 1312.3 ± 258.4 | 111.4 ± 37.4 | 62.8 ± 8.9 |
| 6 | 1477.3 ± 111.1 | 117.8 ± 13.5 | 208.0 ± 36.5 |
| 7 | nd | nd | nd |
| 8 | 1522.2 ± 159.3 | 107.8 ± 15.4 | 194.5 ± 18.8 |

Key to Table 17
— indicates no data as no mice survived
nd indicates no data recorded These results show that testicular tissue was the most sensitive to the effect of irradiation. Administration of PHA prior or after irradiation had less effect on testicular growth.

Treatments 1–3, show low survival after irradiation. The results for treatments 4 & 5 suggest a dose dependent increase in small intestine weight correlated with the time the animals were maintained on PHA containing diet prior to irradiation. The average weight of the spleen tissue from treatments 4 & 5 was similar to that of the controls.

This example demonstrates that irradiation severely compromises animal viability and dietary manipulations can be used to modify the extent to which irradiation compromises viability. Fasting prior to irradiation does not confer protection against irradiation effects, indeed it may be detrimental. Dietary PHA had no detrimental effect on the parameters measured (groups 7 & 8 data compared to group 6) and testicular tissue, of those studied, was the most sensitive to irradiation damage, in terms of weight loss. In the example described, pre-dosing with PHA conferred protection against radiation damage, the degree of which appeared dependant on the time of PHA dosing.

Example 10

Preparation of lectin from the bark of Robinia pseudoacacia

The Robinia bark lectins may be prepared essentially as described by Van Damme et al., (1995 a) from partially purified bark extracts on immobilised fetuin.

Bark tissue was homogenised in 20 mM acetic acid containing 200 mg/l ascorbic acid (10 ml/g fresh weight) using a blender. The homogenate was squeezed through cheesecloth, adjusted to pH 5.0 (with 1M NaOH), and centrifuged for 10,000 g for 10 minutes. The resulting supernatant was filtered through glass wool to remove floating particles. After adding 1.5 g/l $CaCl_2$, the extract was brought to pH 9.0 (with 1M NaOH) and kept overnight at 4° C. The resulting precipitate was removed by centrifugation and the cleared extract adjusted to pH 3.8 with 1 m HCl. After standing overnight again at 4° C., the extract was cleared by centrifugation and adjusted to pH 7.0 with 1M NaOH and brought to 1M ammonium sulphate by adding the solid salt. The solution was then degassed and recentrifuged. The cleared supernatant was loaded onto a fetuin agarose column equilibrated with 1M ammonium sulphate (pH 7.0). After passing the extract, the column was washed with ammonium sulphate until the $A_{280}$ fell below 0.01. The lectin was then desorbed with 20 mM diaminopropane (pH 11). The desorbed lectin was adjusted to pH 7.0 with 1M HCl and bought to 1M ammonium sulphate by adding the solid salt. After centrifuging at 15,000 g for 20 minutes, the supernatant was loaded on a column of phenyl-Sepharose equilibrated with 1M ammonium sulphate. Impurities were removed by washing with 1M ammonium sulphate and the lectins desorbed using a linear gradient of 1M ammonium sulphate to water. Fractions were collected and the $A_{280}$ determined to identify those containing lectin.

It is known that the bark lectin is produced by Robinia pseudoacacia in response to shortening day length i.e. the onset of winter. By using bark material in winter, yields of lectin in the region of 10 mg/g may be attained.

Characterisation of lectins from the bark of Robinia pseudoacacia

The lectins from the bark of Robinia pseudoacacia can be characterised further using ion exchange chromatography, gel filtration and in vitro cell agglutination assays. Such methods are well known in the art and are described in Van Damme et al 1995a and b.

Animal management

Thirty five young male Hooded Lister (Rowett Strain) rats (19 days old weighing 30–40 g) were housed individually in grid bottom cages. The animals were fed a high quality semi-synthetic diet containing 10% lactalbumin protein (Table 1).

Diet and water was freely available at all times except on day 19 when the amount of food offered was restricted to 10 g/rat. At 19 days, rat weights were 100–104 g.

Dietary protocol

The animals were split into five groups and maintained on the following dietary protocol (Table 17a)

TABLE 17a

| Dietary protocol | |
|---|---|
| Treatment | Dietary protocol |
| 1 | LA 3d, inject 5-FU, LA 6d |
| 2 | 25 mg/kg RPA 3d, inject 5-FU, LA 6d |
| 3 | 50 mg/kg RPA 3d, inject 5-FU, LA 6d |
| 4 | 100 mg/kg RPA 3d, inject 5-FU, LA 6d |
| 5 | 100 mg/kg RPA 3d, LA 6d |

Key
LA = lactalbumin
RPA = Robinia pseudoacacia lectin
5-FU = 5-Fluorouracil

The rats were pair fed for the first three days and then fed ab libitum post 5-FU injection.

Administration of RPA

Animals pre-dosed with RPA were given the equivalent of 25, 50 or 100 mg/kg body weight RPA (Table 17a) in 0.9% saline by gavage. The animals were pre-dosed for three consecutive days prior to the 5-FU injection.

Administration of saline

Animals not pre-dosed with RPA were administered with 1 ml 0.9% saline by gavage.

Administration of 5-FU 300 mg of 5-fluorouracil was stirred in 14 ml of distilled water. 1M NaOH was added slowly until the 5-FU had dissolved. The solution was made up to a final volume of 20 ml. The final pH of the solution was 8.3. A dose of 150 mg/kg body weight was administered to the animal by intraperitoneal injection. Immediately after the injection, the rats were offered 15 g of the control diet.

The ability of orally ingested lectins from Robinia pseudoacacia to protect rats from a high dose of chemotherapy, and in particular its tissue protectant effect on the gut was investigated.

Five groups, each consisting of 5 rats were fed on the standard diet containing lactalbumin (Table 1). One group of rats were fed 8 g per day of standard diet for three days and then injected with 5-FU at 150 mg/kg body weight (Table 17a). Three groups of animals were gavaged daily with 25, 50 or 100 mg/kg/day body weight Robinia pseudoacacia lectin (RPA) for three days and then injected with 150 mg/kg 5-FU. The remaining group of animals were pre-dosed with 100 mg/kg body weight RPA and then returned to LA containing diet without injection of 5-FU. After injection with 5-FU, the animals were returned to LA containing diet ad lib. The animals were sacrificed 7 days after the start of the experiment, the carcass dissected and the small intestine, jejunum and ileum wet weights recorded. The results are shown in Table 17b.

TABLE 17b

The affect of pre-dosing with Robinia pseudoacacia lectin for 3 days on the small intestino, jejunum and ileun wet weights (g).

| Treatment | Dosing regime | Small Intestine (g) | Jejunum (g) | Ileum (g) |
|---|---|---|---|---|
| 1 | LA + 5-FU | 5.62 | 1.0 | 1.0 |
| 2 | 25 mg/kg RPA + 5-FU | 5.41 | 1.03 | 0.98 |
| 3 | 50 mg/kg RPA + 5-FU | 5.74 | 1.12 | 1.08 |
| 4 | 100 mg/kg RPA + 5-FU | 6.33 | 1.27 | 1.12 |
| 5 | 100 mg/kg RPA | 6.99 | 1.27 | 1.17 |

The results show a dose-dependent increase in wet weight for all tissues examined with increasing dose of RPA. Thus, pre-dosing with RPA was able to protect tissues of the small intestine, jejunum and ileum from damage induced by 5-FU. Pre-dosing with 100 mg/kg RPA (treatment 4) gave the best tissue prtectant effect when compared to the animals fed lactalbumin alone (treatment 1). Animals pre-dosed with 100 mg/kg RPA and injected with 5-FU (treatment 4) had similar small intestine, jejunum and ileum wet weights to animals fed 100 mg/kg RPA alone (treatment 5).

Visual inspection of the small intestine, jejunum and ileum indicated that animals treated with 5-FU alone (treatment 1) had no, or a very thin mucosal layer on the gut tissue. Animals treated with 5-FU and RPA however had healthy looking gut tissue with a normal mucosal layer.

This example demonstrates that oral administration of *Robinia pseudoacacia* lectin (RPA) before injection with 5-FU gave significant tissue protective effect on the small intestine, jejunum and ileum.

Example 11

Preparation of $A_4$ and $B_4$ RPA bark lectin isotypes

The $A_4$ and $B_4$ homotetramer isotypes may be prepared using a step gradient ion exchange chromatography method. A 100 ml Hyper-D S column (BioSepra) was equilibrated with five column volumes of 50 mM sodium acetate pH 4.75. Freeze dried RPA lectin (obtained as described in the above preparation) was dissolved in acetate buffer (50 mM sodium acetate, pH 4.75) and centrifuged for 10 minutes at 20,000 g. The clarified supernatant was applied to the column and the column subsequently washed with acetate buffer at a flow rate of 3 ml/min. A step gradient was constructed using 50 mM sodium acetate pH 4.75+NaCl. The NaCl was added in increasing concentrations in 5, 7, 9, 12 and 100% step gradients. The fractions containing lectin were selected by measuring the absorbance at 280 nM. The $A_4$ tetramer was eluted in the 5.7% salt fraction and the $B_4$ tetramer in the 9–12% salt fraction.

The fractions containing pure $A_4$ or $B_4$ were confirmed using conventional PAGE and SDS-PAGE methods.

All publications mentioned herein above are hereby incorporated in their entity by reference.

While the forgoing invention has been described in some detail for purposes of clarity and understanding, it will be appreciated by one skilled in the art from a reading of this disclosure that various changes in form and detail can be made without departing from the true scope of the invention and appended claims.

References

Archimund, E. & Thomas, X (1994). Administration of cytotoxic agents by continuous infusion in the therapy of acute myeloid leukemia. Journal of Infusional Chemotherapy, 4, 3–8.

Au, E., Koo, W. H., Tan, E. H. & Ang, P. T. (1996). A Phase II trial of etoposide, leucovorin and 5-Fluorouracil (ELF) in patients with advanced gastric cancer. Journal of Chemotherapy, 8, 300–303.

Banach M., Zaremba S., Sadouska M. (1983). Disturbances of liver and muscle glycogen level as well as blood glucose level in mice following administration of lectin extracted from *Robinia pseudoacacia*. Folia Biol. (Krakow) Vol 31, pp 177–186.

Bardocz, S., Grant, G., Ewen, S. W. B., Duguid, T. J., Brown, D. S., Englyst, K. & Pusztai, A. (1995). Reversible effect of Phytohaemagglutinin on the growth and metabolism of the rat gastrointestinal tract. Gut, 37, 353–360.

Bardocz, S., Brown, D. S., Grant, G., Pusztai, A., Stewart, J. C. & Palmer, R. M. (1992). Effect of the β-adrenoreceptor agonist clenbuterol and phytohaemagglutinin on growth, protein synthesis and polyamine metabolism of tissues of the rat. British Journal of Pharmacology 106, 476–482.

Carvalho, A. F. F. U. de, (1993) Dietary kidney bean lectins affect insulin levels, change gene expression and modulate metabolism. Ph.D. thesis; University of Aberdeen.

Dieras, v & Pouillart, P. (1995). Infusional chemotherapy with new drugs: Taxanes, vinorelbine and topoisomerase I inhibitors. Journal of Infusional Chemotherapy, 5, 191–192.

Denekamp, J. (1996). The broad spectrum of preclinical radiobiology: British contributions. International Journal of Radiation Oncology, Biology & Physics, 36, 497–509.

Duverger, E. and Delmotte, F. M. Purification of lectins from *Robinia pseudoacacia* L. root-tips. Plant Science 123.9–18, (1997).

Erkisi, M., Erkurt, E., Ozbarlas, S., Burgut, R., Doran, F. & Seyrek, E. (1996). The use of recombinant human granulocyte colony-stimulating factor in combination with single or fractionated doses of isofamide and doxorubicin in patients with soft tissue sarcoma. Journal of Chemotherapy, 8, 224–228.

Fleischmann, G. and Rudiger, H. (1986). Isolation, resolution and partial characterisation of two *Robinia pseudoacacia* seed lectins. Biol. Chem. Hoppe-Seyler, 367, 27–32.

Gietl, C. and Ziegler H., Biochem, Physiol. Planzen 175, 58–66 (1080)

Lehninger, A. L., Nelson, D. L. & Cox, M. C. (1997). Principles of biochemistry, Worth Publishers, New York.

Grant, G., McKenzie, N. H., Watt, W. B., Stewart, J. C., Dorward, P. M. & Pusztai, A. (1986) Nutritional evaluation of soya beans (*Glycine max*): Nitrogen balance and fractionation studies. Journal of the Science of Food and Agriculture, 37, 1001–1010.

Grant, G., Oliveira, J. T. A., de, Dorward, P. M., Annand, M. G., Waldron, M. & Pusztai, A. (1987). Metabolic and hormonal changes in rats resulting from consumption of kidney bean (*Phaseolus vulgaris*) or soyabean (*Glycine max*). Nutritional Reports International 36, 763–772.

Grant, G., Dormand, P. M. and Pusztai, A. (1993) Pancreatic enlargement is evident in rats Fed diets containing raw soybean (*Glycine max*) or cowpeas (*Vigna unguiculata*) but not those fed diets dased on kidney beans (*Phaseolus vulgaris*) or lupinseed (*Luinas augustlfalinus*). Journal of Nutrition 123 2207–2215.

Gupta, Y. P. (1987) Nutritive value of soybean. International Journal of Tropical Agriculture, 5, 247–279.

Hajos, Gy., Gelencser, E., Pusztai, A., Grant, G., Sakhri, M. & Bardocz, S. (1995) Biological effects and survival of trypsin inhibitors and the agglutinin from soybean in the small intestine of the rat. Journal of Agricultural and Food Chemistry, 43, 165–170.

Harboe, N. & Inglid, A. (1973) Immunization, isolation of immunoglobulins, estimation of antibody titre. In A Manual of Quantitative Immunoelectrophoresis, Methods and Applications; (N. H. Axelsen, J. Kroll & B. Weeke, editors) Scandinavian Journal of Immunology, (Suppl. 1), pp. 161–164.

Isacoff, W. H., Frederick, R., Kuchenbecker, S. L., Jacobs, A. D. & Taylor, O. (1994). Continuous infusion 5-fluorouracil given with calcium luucovorin, dipyridamole, and Mitomycin-C in patients with advancer colerectal carcinoma: A Phase II trial. Journal of Infusional Chemotherapy, 4, 107–111

Liener, I. E. (1994) Implications of antinutritional components in soybean foods. Critical Reviews in Food Science and Nutrition, 34, 31–67.

Macrae, J. C., Bruce, L. A., Hovell, F. B. de B., Hart, I. C., Inkster, J., Walker, A. & Atkinson, T. (1991). Influence of protein nutrition on the response of growing lambs to exogenous bovine growth hormone. Journal of Endocrinology 130, 53–61.

Nishiguchi, M., Yoshida, K., Sumizono, T. & Tazaki, T. (1997). Studies by site directed mutagenesis of the carbohydrate binding properties of a bark lectin from *Robinia pseudoacacia*. FEBS Letters, 403, 294–298.

Palmer, R. M., Pusztai, A., Bain, P. & Grant, G. (1987). Changes in rates of tissue protein synthesis in rats induced in vivo by consumption of kidney bean lectins. Comparative Biochemistry and Physiology 88C, 179–183.

Paulsen, F., Hoffmann, W., Kortmann, R. D., Porschen, R. & Bamberg, M. (1996). Akute gastrointestinal Nebenwirkungen in der Radio-onkologie—Was ist gesichert in der Therapie?. Strahlenther. Onkol. 172, 53–56 (Nr 2).

Podolsky, D. K. (1993). Regulation of intestinal epithelial proliferation: a few answers, many questions. Am. J. Physiol. 264, pp G179–G186.

Pusztai, A. (1991). Plant Lectins. Cambridge: Cambridge University Press.

Pusztai, A. & Palmer, R. M. (1977). Nutritional evaluation of kidney bean (*Phaseolus vulgaris*): the toxic principle. Journal of the Science of Food and Agriculture 28, 620–623.

Pusztai, A. (1993) Dietary lectins are metabolic signals for the gut and modulate immune and hormone functions. Eur J of Clin Nut, 47, 691–699.

Pusztai, A., Ewan, S. W. B., Grant G., Peumans, W. J., Van Damme, E. J. M., Coates, M. E. and Bardocz, S. (1995). Lectins and also bacteria modify the glycosylation of gut receptors in the rat. Glycoconjugate Journal, 12, 22–35.

Pusztai, A., Greer, F. & Grant, G. (1989). Specific uptake of dietary lectins into the systemic circulation of rats. Biochemical Society Transactions 17, 481–482.

Pusztai, A., Grant, G., Spencer, R. J., Duguid, T. J., Brown, D. S., Ewen, S. W. B., Peumans, W. J., Van Damme, E. J. M. & Bardocz, S. (1993). Kidney bean lectin-induced *Escherichia coli* overgrowth in the small intestine is blocked by GNA, a mannose-specific lectin. Journal of Applied Bacteriology 75, 360–368.

Rackis, J. J., Wolf, W. J. & Baker, E. C. (1986) Protease inhibitors in plant foods; content and inactivation. In Nutritional and Toxicological Significance of Enzyme Inhibitors in Foods (M. Friedman, editor) Plenum Press, New York, pp. 299–331.

Raedler, A., Boehle A., Otto, U. & Raedler, E. (1982). Differences of glycoconjugate exposed on hypernephroma and normal kidney cells. Journal of Urology, 128, 1109–1113.

Sabeur, G., Wantyghem, J. & Schuller, E. (1986). Stimulation of 2',3'-cyclic nucleotide 3'-phosphodiesterase in human lymphocytes by *Robinia pseudoacacia* lectin. Biochemie, 68, 581–585.

Sharif, A., Brochier, J. & Bourrillon, R. (1977). Specific activation of Human T lyphocytes by *Robinia pseudoacacia* seeds lectin. Cellular Immunology, 31, 302–310.

Sharif, A., Lethibichthuy, J., Brochier, J., Goussalt, Y. & Bourrillon, R. (1978). Activation of human B lymphocytes induced by *Robinia pseudoacacia* lectin in the presence of T cells. Immunology, 35, 643–649.

Sparano, J. A. & Wiernik, P. H. (1994). Infusional cyclophosphamide-based therapy for the treatment of lymphoma. Journal of Infusional Chemistry, 4, 28–32.

Steel, G. G. (1996). From targets to genes: a brief history of radiosensitivity. Phys Med. Biol., 41, 205–222.

Trinder, P. (1967). Determination of glucose in blood using glucose oxidase with an alternative oxygen acceptor. Annals Clinical Biochemistry 6, 24–27.

Van Damme, E. J. M., Barre, A., Smeets, K., Torrekens, S., Van Leuren, F., Rouge, P., and Peumans, W. J. (1995a). The bark of *Robinia pseudoacacia* contains a complex mixture of lectins. Plant physiol, 107, 833–843.

Van Damme, E. J. M., Barre, A., Rouge, P., Van Leuven, F., and Peumaas, W. (1995b). The seed lectins of black locust (*Robinia pseudoacacia*) are encoded by two genes which differ from the bark lectin genes. Plant Molecular Biology, 29, 1197–1210.

Van Halteren, H. K., Gortzak, E., Taal, B. G., Helmerhorst, Th, J, M., Aleman, B. M. P., Hart, A. A. M. & Zoetmulder, F. A. N. (1993). Surgical intervention for complications caused by late radiation damage of the small bowel: a retrospective analysis. European Journal of Surgical Oncology, 19, 336–341.

Wantyghem, J., Goulut, C., Frenoy, J. P., Turpin, E. and Goussault, Y. (1986). Purification and characterisation of *Robinia pseudoacacia* seed lectins. A re-investigation. Biochem J., 237, 483–489.

Yeoh, E., Horowitz, M., Russo, A., Muecke, T., Ahmad, A. & Chatterton, B. (1993). International Journal of Radiation Oncology, Biology & Physics, 26, 229–237.

Yoshida, K., Baba, K., Yamamoto, N. & Tazaki, K (1994). Cloning of a lectin cDNA and seasonal changes in levels of the lectin and its mRNA in the inner bark of *Robinia pseudoacacia*. Plant Mol. Biol. (1994), 25, 845–853.

What is claimed is:

1. A method for the prophylaxis or treatment of mucosal cell damage caused by a cell-damaging agent selected from the group consisting of chemotherapeutic agents, radiotherapy, inorganic or organic chemicals, toxins, acids, alkali, radiation and free radicals, comprising administering to an individual in need of such prophylaxis or treatment an amount of lectin effective to promote mucosal cell proliferation thereby counteracting said damage, and further administering a cytoprotectant therewith.

2. A method according to claim 1, wherein the damage is caused by one or more of gut lesions or mucositis.

3. A method according to claim 1, wherein the damage is caused by inflammatory bowel disease or irritable bowel syndrome.

4. A method according to claim 1, for the prophylaxis or treatment of one or more cells or tissues, selected from the group consisting of damaged mammalian cells, damaged mammalian tissue, damaged human cells and damaged human tissue.

5. A method according to claim 4, wherein the cells and/or tissues are one or more selected from the group consisting of mucosal coverings of the gut, the mouth, the nasal passage, the oesophagus, the stomach, the lung, the small intestine, the large intestine, and epithelial tissue and other mucosal cells and tissues.

6. A method according to claim 1, wherein the lectin is from one or more plants selected from the group consisting of kidney bean, soya bean, Jack bean, *Robinia pseudoacacia*, wheat germ, lotus seed, onion, lentil, tomato and potato.

7. A method according to claim 1, wherein the lectin is from *Robinia pseudoacacia*.

8. A method as claimed in claim 1, wherein the lectin comprises bark, seed, root, root nodule, phloem, wood or leaf lectin, or a combination of two or more thereof from *Robinia pseudoacacia*.

9. A method as claimed in claim 1, wherein the lectin comprises at least one polypeptide subunit from a *Robinia pseudoacacia* lectin.

10. A method as claimed in claim 1, wherein the lectin comprises a dimer, trimer or tetramer of lectin subunits, or a combination of two or more thereof from *Robinia pseudoacacia*.

11. A method as claimed in claim 1, wherein the lectin comprises a tetramer of four bark polypeptide a subunits or four bark polypeptide b subunits or a mixture of a and b subunits from *Robinia pseudoacacia*.

12. A method as claimed in claim 1, wherein administration is by one or more routes selected from the group consisting of by mouth, rectally and parenterally.

13. A method for the reduction and/or treatment of damage caused by a cell-damaging agent selected from the group consisting of chemotherapeutic agents, radiotherapy, inorganic or organic chemicals, toxins, acids alkali, radiation and free radicals, comprising administering to an individual in need of such treatment an amount of lectin effective to promote cell growth thereby counteracting said damage, and further administering a cytoprotectant therewith.

14. A method according to claim 13, for the reduction and/or treatment of one or more cells or tissues selected from the group consisting of damaged mammalian cells, damaged mammalian tissue, damaged human cells and damaged human tissue.

15. A method according to claim 14, wherein the cells and/or tissues are one or more selected from the group consisting of mucosal coverings of the gut, the mouth, the nasal passage, the oesophagus, the stomach, the lung, the small intestine, the large intestine, and epithelial tissue and other mucosal cells and tissues, bone marrow, spleen, blood generating cells, blood tissue, thymus, hair-producing tissue, eye tissue and testicular/prostate tissue.

16. A method according to claim 13, wherein the lectin is from one or more plants selected from the group consisting of kidney bean, soya bean, Jack bean, *Robinia pseudoacacia*, wheat germ, lotus seed, onion, lentil, tomato and potato.

17. A method according to claim 13, wherein the lectin is from *Robinia pseudoacacia*.

18. A method as claimed in claim 13, wherein the lectin comprises bark, seed, root, root nodule, phloem, wood or leaf lectin, or a combination of two or more thereof from *Robinia pseudoacacia*.

19. A method as claimed in claim 13, wherein the lectin comprises at least one polypeptide subunit from a *Robinia pseudoacacia* lectin.

20. A method as claimed in claim 13, wherein the lectin comprises a dimer, trimer or tetramer of lectin subunits, or a combination of two or more thereof from *Robinia pseudoacacia*.

21. A method as claimed in claim 13, wherein the lectin comprises a tetramer of four bark polypeptide a subunits or four bark polypeptide b subunits or a mixture of a and b subunits from *Robinia pseudoacacia*.

22. A method as claimed in claim 13, wherein administration is by one or more routes selected from the group consisting of by mouth, rectally and parenterally.

23. A method according to claim 1, wherein the cytoprotectant is one or more selected from the group consisting of a radiosensitiser, a chemoprotectant, and growth factor.

24. A method according to claim 1, wherein the cytoprotectant is one or more selected from the group consisting of vitamin K mimetic, gadolinium texaphyrin and iobenguane.

25. A method according to claim 1, wherein the cytoprotectant is one or more selected from the group consisting of Sulcraphate, cysteine, cysteamine, Ethyol, balazipone, dosmalfate, WR 3689 (2-[[3-methylamino)propyl]amino] ethanethiol dihydrogen phosphate ester, AD 20 (2-[[2-methoxyphenyl)acetyl]amino]-2-propenoic acid and a nitroxide antioxidant.

26. A method according to claim 1, wherein the cytoprotectant is one or more selected from the group consisting of granulocyte colony-stimulating factor, granulocyte-macrophage colony-stimulating factor, Erythropoietin, epidermal growth factor, keratinocyte growth factor, transforming growth factor, an interleukin, insulin-like growth factor, nerve growth factor, platelet-derived growth factor, Bombesin, Relaxin, Calcitonin, colustrum-derived growth factor, amlexanox, amoxanox, protegrin, pilocarpine hydrochloride, stem cell factor, thrombopoietin, steel factor, an interferon and a cytokine.

27. A method according to claim 13, wherein the cytoprotectant is one or more selected from the group consisting of a radiosensitiser, a chemoprotectant and growth factor.

28. A method according to claim 13, wherein the cytoprotectant is one or more selected from the group consisting of vitamin K mimetic, gadolinium texaphyrin and iobenguane.

29. A method according to claim 13, wherein the cytoprotectant is one or more selected from the group consisting of Sulcraphate, cysteine, cysteamine, Ethyol, balazipone, dosmalfate WR 3689 (2-[[3-methylamino)propyl]amino] ethanethiol dihydrogen phosphate ester, AD 20 (2-[[2-methoxyphenyl)acetyl]amino]-2-propenoic acid and a nitroxide antioxidant.

30. A method according to claim 13, wherein the cytoprotectant is one or more selected from the group consisting of granulocyte colony-stimulating factor, granulocyte-macrophage colony-stimulating factor, Erythropoietin, epidermal growth factor, keratinocyte growth factor, transforming growth factor, an interleukin, insulin-like growth factor, nerve growth factor, platelet-derived growth factor, Bombesin, Relaxin, Calcitonin, colustrum-derived growth factor, amlexanox, amoxanox, protegrin, pilocarpine hydrochloride, stem cell factor, thrombopoietin, steel factor, an interferon and cytokine.

31. A method according to claim 1, wherein the lectin is administered in a concentration of from 0.3 g to 0.1 μg per kg body weight per day.

32. A method according to claim 13, wherein the lectin is administered in a concentration of from 0.3 g to 0.1 μg per kg body weight per day.

33. A method to promote mucosal cell proliferation in an individual in need thereof, comprising administering to said individual an amount of a lectin effective to promote mucosal cell proliferation.

34. A method according to claim 33, wherein the mucosal cell proliferation is associated with one or more conditions, selected from the group consisting of gut lesions and mucositis.

35. A method according to claim 33, wherein the mucosal cell proliferation is associated with one or more conditions, selected from the group consisting of inflammatory bowel disease and irritable bowel syndrome.

36. A method according to claim 33, wherein the mucosal cell proliferation is associated with damage caused by a cell-damaging agent.

37. A method according to claim 33, wherein the mucosal cell proliferation is in one or more cells or tissues, selected from the group consisting of damaged mammalian cells, damaged mammalian tissue, damaged human cells and damaged human tissue.

38. A method according to claim 33, wherein the proliferation is in one or more tissues selected from the group consisting of mucosal coverings of the gut, the mouth, the nasal passage, the oesophagus, the stomach, the lung, the small intestine, the large intestine, and epithelial tissue and other mucosal cells and tissues.

39. A method according to claim 36, wherein the cell-damaging agent is one or more selected from the group consisting of radiotherapy and a chemotherapeutic agent.

40. A method according to claim 36, wherein the cell-damaging agent is one or more selected from the group consisting of X-ray, gamma ray, proton source, neutron source, α-emitter, and β-emitter.

41. A method according to claim 36, wherein the cell-damaging agent is one or more selected from the group consisting 5-fluorouracil, Cisplatin, doxorubicin, methotrexate and taxol.

42. A method according to claim 33, wherein the lectin is from one or more plants selected from the group consisting of kidney bean, soya bean, Jack bean, *Robinia pseudoacacia*, wheat germ, lotus seed, onion, lentil, tomato and potato.

43. A method according to claim 33, wherein the lectin is from *Robinia pseudoacacia*.

44. A method as claimed in claim 33, wherein the lectin comprises bark, seed, root, root nodule, phloem, wool or leaf lectin, or a combination of two or more thereof from *Robinia pseudoacacia*.

45. A method as claimed in claim 33, wherein the lectin comprises at least one polypeptide subunit from a *Robinia pseudoacacia* lectin.

46. A method as claimed in claim 33, wherein the lectin comprises a dimer, trimer or tetramer of lectin subunits, or a combination of two or more thereof from *Robinia pseudoacacia*.

47. A method as claimed in claim 33, wherein the lectin comprises a tetramer of four bark polypeptide a subunits or four bark polypeptide b subunits or a mixture or a and b subunits from *Robinia pseudoacacia*.

48. A method as claimed in claim 33, wherein administration is by one or more routes, selected from the group consisting of by mouth, rectally and parenterally.

49. A method for the prophylaxis or treatment of mucosal cell damage caused by a cell damaging agent selected from the group consisting of chemotherapeutic agents, radiotherapy, inorganic or organic chemicals, toxins, acids, alkali, radiation and free radicals, comprising administering to an individual in need of such prophylaxis or treatment an amount of lectin effective to promote mucosal cell proliferation, thereby counteracting said damage.

50. A method according to claim 49, wherein the prophylaxis or treatment of mucosal cell damage is associated with one or more conditions, selected from the group consisting of gut lesions and mucositis.

51. A method according to claim 49, wherein the prophylaxis or treatment of mucosal cell damage is associated with one or more conditions, selected from the group consisting of inflammatory bowel disease and irritable bowel syndrome.

52. A method according to claim 49, for the prophylaxis or treatment of mucosal cell damage of one or more cells or tissues, selected from the group consisting of damaged mammalian cells, damaged mammalian tissue, damaged human cells and damaged human tissue.

53. A method according to claim 49, wherein the prophylaxis or treatment is of one or more tissues selected from the group consisting of mucosal coverings of the gut, the mouth, the nasal passage, the oesophagus, the stomach, the lung, the small intestine, the large intestine, and epithelial tissue and other mucosal cells and tissues.

54. A method according to claim 49, wherein the radiotherapy is one or more selected from the group consisting of X-ray, gamma ray, proton source, neutron source, α-emitter, and β-emitter.

55. A method according to claim 49, wherein the chemotherapeutic agent is one or more selected from the group consisting 5-fluorouracil, Cisplatin, doxorubicin, methotrexate and taxol.

56. A method according to claim 49, wherein the lectin is from one or more plants selected from the group consisting of kidney bean, soya bean, Jack bean, *Robinia pseudoacacia*, wheat germ, lotus seed, onion, lentil, tomato and potato.

57. A method according to claim 49, wherein the lectin is from *Robinia pseudoacacia*.

58. A method as claimed in claim 49, wherein the lectin comprises bark, seed, root, root nodule, phloem, wood or leaf lectin, or a combination of two or more thereof from *Robinia pseudoacacia*.

59. A method as claimed in claim 49, wherein the lectin comprises at least one polypeptide subunit from a *Robinia pseudoacacia* lectin.

60. A method as claimed in claim 49, wherein the lectin comprises a dimer, trimer or tetramer of lectim subunits, or a combination of two or more thereof from *Robinia pseudoacacia*.

61. A method as claimed in claim 49, wherein the lectin comprises a tetramer of four bark polypeptide a subunits or four bark polypeptide b subunits or a mixture of a and b subunits from *Robinia pseudoacacia*.

62. A method as claimed in claim 49, wherein administration is by one or more routes selected from the group consisting of by mouth, rectally and parenterally.

63. A method for the reduction and/or treatment of damage caused by a cell damaging agent selected from the group consisting of chemotherapeutic agents, radiotherapy, inorganic or organic chemicals, toxins, acids, alkali, radiation and free radicals comprising administering to an individual in need of such treatment an amount of lectin effective to promote cell growth thereby counteracting said damage.

64. A method according to claim 63 for the reduction and/or treatment of one or more cells or tissues selected from the group consisting of damaged mammalian cells, damaged mammalian tissue, damaged human cells and damaged human tissue.

65. A method according to claim 63, wherein the cells and/or tissue are one or more selected from the group consisting of mucosal coverings of the gut, the mouth, the nasal passage, the oesophagus, the stomach, the lung, the small intestine, the large intestine, and epithelial tissue and other mucosal cells and tissues, bone marrow, spleen, blood generating cells, blood tissue, thymus, hair-producing tissue, eye tissue and testicular/prostate tissue.

66. A method according to claim 63, wherein the lectin is from one or more plants selected from the group consisting of kidney bean, soya bean, Jack bean, *Robinia pseudoacacia*, wheat germ, lotus seed, onion, lentil, tomato and potato.

67. A method according to claim 63, wherein the lectin is from *Robinia pseudoacacia*.

68. A method as claimed in claim 63, wherein the lectin comprises bark, seed, root, root nodule, phloem, wood or leaf lectin, or a combination of two or more thereof from *Robinia pseudoacacia*.

69. A method as claimed in claim 63, wherein the lectin comprises at least one polypeptide subunit from a *Robinia pseudoacacia* lectin.

70. A method as claimed in claim 63, wherein the lectin comprises a dimer, trimer or tetramer of lectin subunits, or a combination of two or more thereof from *Robinia pseudoacacia*.

71. A method as claimed in claim 63, wherein the lectin comprises a tetramer of four bark polypeptide a subunits or four bark polypeptide b subunits or a mixture of a and b subunits from *Robinia pseudoacacia*.

72. A method as claimed in claim 63, wherein administration is by one or more routes selected from the group consisting of my mouth, rectally and parenterally.

73. A method according to claim 33, wherein the lectin is administered in a concentration of from 0.3 g to 0.1 μg per kg body weight per day.

74. A method according to claim 49, wherein the lectin is administered in a concentration of from 0.3 g to 0.1 μg per kg body weight per day.

75. A method according to claim 63, wherein the lectin is administered in a concentration of from 0.3 g to 0.1 μg per kg body weight per day.

* * * * *